(12) United States Patent
Cai et al.

(10) Patent No.: US 10,981,942 B2
(45) Date of Patent: *Apr. 20, 2021

(54) CRYSTALLINE FORM OF BENZYLBENZENE SGLT2 INHIBITOR

(71) Applicant: THERACOS SUB, LLC, Marlborough, MA (US)

(72) Inventors: Mengzhuang Cai, Shanghai (CN); Qian Liu, Shanghai (CN); Ge Xu, Shanghai (CN); Binhua Lv, Shanghai (CN); Brian Seed, Boston, MA (US); Jacques Roberge, Princeton, NJ (US)

(73) Assignee: THERACOS SUB, LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/694,642

(22) Filed: Nov. 25, 2019

(65) Prior Publication Data

US 2020/0239510 A1   Jul. 30, 2020

Related U.S. Application Data

(60) Continuation of application No. 15/804,074, filed on Nov. 6, 2017, now Pat. No. 10,533,032, which is a division of application No. 14/627,693, filed on Feb. 20, 2015, now Pat. No. 9,834,573, which is a division of application No. 13/158,724, filed on Jun. 13, 2011, now Pat. No. 8,987,323.

(30) Foreign Application Priority Data

Jun. 12, 2010 (WO) ................ PCT/CN2010/073865

(51) Int. Cl.
| | | |
|---|---|---|
| *A61K 31/351* | (2006.01) | |
| *C07D 309/10* | (2006.01) | |
| *A61P 3/10* | (2006.01) | |
| *C07H 1/06* | (2006.01) | |
| *C07H 7/04* | (2006.01) | |

(52) U.S. Cl.
CPC ............ *C07H 1/06* (2013.01); *A61K 31/351* (2013.01); *A61P 3/10* (2018.01); *C07D 309/10* (2013.01); *C07H 7/04* (2013.01)

(58) Field of Classification Search
None
See application file for complete search history.

(56) References Cited

U.S. PATENT DOCUMENTS

| | | | |
|---|---|---|---|
| 5,663,377 A | 9/1997 | Curley, Jr. et al. | |
| 6,069,238 A | 5/2000 | Hitchcock et al. | |
| 6,414,126 B1 | 7/2002 | Ellsworth et al. | |
| 6,515,117 B2 | 2/2003 | Ellsworth et al. | |
| 6,555,519 B2 | 4/2003 | Washburn | |
| 6,683,056 B2 | 1/2004 | Washburn et al. | |
| 6,774,112 B2 | 8/2004 | Gougoutas | |
| 6,936,590 B2 | 8/2005 | Washburn et al. | |
| 7,022,725 B2 | 4/2006 | Momose et al. | |
| 7,094,763 B2 | 8/2006 | Rybczynski et al. | |
| 7,371,732 B2 | 5/2008 | Eickelmann et al. | |
| 7,375,090 B2 | 5/2008 | Himmelsbach et al. | |
| 7,375,213 B2 | 5/2008 | Deshpande et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,713,938 B2 | 5/2010 | Hmmielsbach | |
| 7,838,498 B2 | 11/2010 | Chen et al. | |
| 7,838,499 B2 | 11/2010 | Chen et al. | |
| 8,106,021 B2 | 1/2012 | Chen et al. | |
| 8,283,454 B2 | 10/2012 | Liou et al. | |
| 8,802,637 B2 | 8/2014 | Chen et al. | |
| 8,987,323 B2 | 3/2015 | Cai et al. | |
| 9,006,403 B2 * | 4/2015 | Liou ................... | A61P 3/00 536/1.11 |
| 9,061,060 B2 | 6/2015 | Seed | |
| 9,834,573 B2 * | 12/2017 | Cai .................... | A61P 3/04 |
| 10,533,032 B2 * | 1/2020 | Cai .................... | A61P 5/48 |
| 2002/0111315 A1 | 8/2002 | Washburn et al. | |
| 2003/0064935 A1 | 4/2003 | Gougoutas | |
| 2003/0087843 A1 | 5/2003 | Washburn | |
| 2003/0114390 A1 | 6/2003 | Washburn et al. | |
| 2004/0138148 A1 | 7/2004 | Fushimi et al. | |

(Continued)

FOREIGN PATENT DOCUMENTS

| | | |
|---|---|---|
| CA | 2539032 A1 | 3/2005 |
| CA | 2548 53 A1 | 7/2005 |

(Continued)

OTHER PUBLICATIONS

Armarego, W.L.F., et al., Purification of Laboratory Chemicals. Published by Elsevier (© 2003); pp. 14-17 and 37.
Banker, G.S. et al., Modern Pharmaceutics, 3rd ed., Marcel Dekker, New York (© 1996); p. 596.
Brittain, H. G. et al., Polymorphism in Pharmaceutical Solids, Chapter 1: Theory and Origin of Polymorphism, pp. 1-10; and Chapter 5: Generation of Polymorphs, Hydrates, Solvates, and Amorphous Solids, pp. 183-225; (© 1999).
Byrn, Stephen et al., "Pharmaceutical Solids: A Strategic Approach to Regulatory Considerationsm" Pharmaceutical Research (Jul. 1995); 12(7):945-954.
Caira, et al., Topics in Current Chemistry: Design of Organic Solids, Chapter: Crystalline Polymorphism of Organize compounds (© 1998); pp. 163-208.

(Continued)

*Primary Examiner* — Eric Olson
(74) *Attorney, Agent, or Firm* — Mintz, Levin, Cohn, Ferris, Glovsky & Popeo, P.C.

(57) ABSTRACT

Provided are crystalline forms of a compound having an inhibitory effect on sodium-dependent glucose cotransporter SGLT2. The invention also provides pharmaceutical compositions, methods of preparing the crystalline compound, and methods of using the crystalline compound, independently or in combination with other therapeutic agents, for treating diseases and conditions which are affected by SGLT or SGLT2 inhibition.

10 Claims, 7 Drawing Sheets

(56) References Cited

U.S. PATENT DOCUMENTS

| | | |
|---|---|---|
| 2004/0138439 A1 | 7/2004 | Deshpande et al. |
| 2004/0259819 A1 | 12/2004 | Frick et al. |
| 2005/0014704 A1 | 1/2005 | Frick et al. |
| 2005/0032712 A1 | 2/2005 | Urbanski |
| 2005/0037980 A1 | 2/2005 | Rybczynski et al. |
| 2005/0187168 A1 | 8/2005 | Eickelmann et al. |
| 2005/0209166 A1 | 9/2005 | Eckhardt et al. |
| 2005/0209309 A1 | 9/2005 | Sato et al. |
| 2005/0233982 A1 | 10/2005 | Himmelsbach et al. |
| 2005/0233988 A1 | 10/2005 | Nomura et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0122126 A1 | 6/2006 | Imamura et al. |
| 2006/0142210 A1 | 6/2006 | Eckhardt et al. |
| 2006/0166899 A1 | 7/2006 | Teranishi et al. |
| 2006/0189548 A1 | 8/2006 | Himmelsbach et al. |
| 2006/0234953 A1 | 10/2006 | Himmelsbach et al. |
| 2006/0234954 A1 | 10/2006 | Urbanski |
| 2006/0235062 A1 | 10/2006 | Neogi et al. |
| 2006/0247179 A1 | 11/2006 | Fushimi et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0072896 A1 | 3/2007 | Khan et al. |
| 2007/0161787 A1 | 7/2007 | Imamura et al. |
| 2007/0185197 A1 | 8/2007 | Fujikura et al. |
| 2007/0197450 A1 | 8/2007 | Fushimi et al. |
| 2007/0249544 A1 | 10/2007 | Himmelsbach et al. |
| 2007/0275907 A1 | 11/2007 | Chen et al. |
| 2008/0004336 A1 | 1/2008 | Gougoutas et al. |
| 2008/0027014 A1 | 1/2008 | Nomura et al. |
| 2008/0132563 A1 | 6/2008 | Kakinuma et al. |
| 2008/0318874 A1 | 12/2008 | Matsuoka et al. |
| 2009/0023913 A1 | 1/2009 | Eckhardt et al. |
| 2009/0030006 A1 | 1/2009 | Kobayashi et al. |
| 2009/0118201 A1 | 5/2009 | Chen et al. |
| 2010/0063141 A1 | 3/2010 | Seed et al. |
| 2010/0222599 A1* | 9/2010 | Liou ............ C07D 309/10 548/532 |
| 2012/0238510 A1 | 9/2012 | Cai et al. |
| 2015/0266915 A1 | 9/2015 | Cai et al. |

FOREIGN PATENT DOCUMENTS

| | | |
|---|---|---|
| CN | 1407990 A | 4/2003 |
| CN | 101754972 A | 6/2010 |
| EP | 9831697 A1 | 7/1998 |
| EP | 1489089 A1 | 12/2004 |
| EP | 1783110 A1 | 5/2007 |
| EP | 1803721 A1 | 7/2007 |
| EP | 1852439 A1 | 11/2007 |
| EP | 1908757 A1 | 4/2008 |
| EP | 2009010 A1 | 4/2008 |
| WO | 01027128 A1 | 4/2001 |
| WO | 01074834 A1 | 10/2001 |
| WO | 01074835 A1 | 10/2001 |
| WO | 02083066 A2 | 10/2002 |
| WO | 03020737 A1 | 3/2003 |
| WO | 03099836 A1 | 12/2003 |
| WO | 2004063209 A2 | 7/2004 |
| WO | 2005021566 A2 | 3/2005 |
| WO | 2005063785 A2 | 7/2005 |
| WO | 2005085237 A1 | 9/2005 |
| WO | 2005092877 A1 | 10/2005 |
| WO | 2006002912 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006064033 A2 | 6/2006 |
| WO | 2006073197 A1 | 7/2006 |
| WO | 2006080421 A1 | 8/2006 |
| WO | 06110654 A1 | 10/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007114475 A2 | 10/2007 |
| WO | 2007136116 A1 | 11/2007 |
| WO | 2008002824 A1 | 1/2008 |
| WO | 2008049923 A1 | 5/2008 |
| WO | 2008069327 A1 | 6/2008 |
| WO | 2008144346 A2 | 11/2008 |
| WO | 2009026537 A1 | 2/2009 |
| WO | 2009035969 A1 | 3/2009 |
| WO | 2010009243 A1 | 1/2010 |
| WO | 2010022313 A2 | 2/2010 |

OTHER PUBLICATIONS

Isaji, M., "Sodium-glucose cotransporter inhibitors for diabetes," Current Opinion in Investigational Drugs, (Apr. 1, 2007); 8(4):285-292.

Morissette, S.L., et al.,"High-throughput crystallization: polymorphs, salts, co-crystals and solvates of pharmaceutical solids," Advanced Drug Delivery Reviews; (2004; accepted Oct. 6, 2003); 56:275-300.

Rodriguez-Spong, et al., "General principles of pharmaceutical solid polymorphism: a supramolecular perspective," Advanced Drug Delivery Reviews, (2004; accepted Oct. 6, 2003); 56:241-274.

Wolff, Manfred E., Burger's Medicinal Chemistry, 5th ed, Part I, John Wiley & Sons (© 1995), pp. 975-977.

International Search Report corresponding to International Application No. PCT/CN2011/075554, dated Sep. 29, 2011; 16 pages.

Office Action corresponding to Colombian Patent Application No. 12.212.81, dated Jan. 14, 2014, 13 pages.

Extended European Search Report corresponding to European Patent Application No. 09808859, dated Aug. 1, 2011.

Extended European Search Report corresponding to EP 11791943.1, dated Oct. 8, 2013; 7 pages.

International Search Report corresponding to International Application No. PCT/US2009/054585, dated Apr. 26, 2010; 4 pages.

International Search Report corresponding to International Application No. PCT/US2008/074058, dated Nov. 17 2008; 2 pages.

International Search Report corresponding to International Application No. PCT/CN2010/073865, dated Mar. 24, 2011.

* cited by examiner

| 2θ | d space (Å) | Intensity (%) |
|---|---|---|
| 5.4 ± 0.1 | 16.509 ± 0.314 | 11 |
| 10.7 ± 0.1 | 8.255 ± 0.078 | 3 |
| 11.2 ± 0.1 | 7.922 ± 0.071 | 47 |
| 11.3 ± 0.1 | 7.817 ± 0.069 | 12 |
| 11.9 ± 0.1 | 7.445 ± 0.063 | 14 |
| 12.9 ± 0.1 | 6.886 ± 0.054 | 100 |
| 14.7 ± 0.1 | 6.035 ± 0.041 | 3 |
| 15.0 ± 0.1 | 5.908 ± 0.039 | 4 |
| 15.5 ± 0.1 | 5.700 ± 0.037 | 56 |
| 16.1 ± 0.1 | 5.494 ± 0.034 | 5 |
| 16.3 ± 0.1 | 5.438 ± 0.033 | 32 |
| 17.8 ± 0.1 | 4.982 ± 0.028 | 75 |
| 18.7 ± 0.1 | 4.744 ± 0.025 | 9 |
| 19.1 ± 0.1 | 4.641 ± 0.024 | 92 |
| 20.0 ± 0.1 | 4.430 ± 0.022 | 50 |
| 20.6 ± 0.1 | 4.320 ± 0.021 | 41 |
| 20.7 ± 0.1 | 4.282 ± 0.021 | 76 |
| 21.2 ± 0.1 | 4.182 ± 0.020 | 35 |
| 21.6 ± 0.1 | 4.121 ± 0.019 | 6 |
| 22.4 ± 0.1 | 3.963 ± 0.018 | 8 |
| 22.8 ± 0.1 | 3.903 ± 0.017 | 42 |
| 23.0 ± 0.1 | 3.870 ± 0.017 | 24 |
| 23.4 ± 0.1 | 3.810 ± 0.016 | 20 |
| 23.6 ± 0.1 | 3.770 ± 0.016 | 29 |
| 23.9 ± 0.1 | 3.725 ± 0.015 | 34 |
| 24.7 ± 0.1 | 3.604 ± 0.014 | 12 |
| 24.9 ± 0.1 | 3.570 ± 0.014 | 9 |
| 25.4 ± 0.1 | 3.506 ± 0.014 | 12 |
| 25.8 ± 0.1 | 3.450 ± 0.013 | 23 |
| 27.0 ± 0.1 | 3.299 ± 0.012 | 2 |
| 27.5 ± 0.1 | 3.240 ± 0.012 | 9 |
| 27.8 ± 0.1 | 3.208 ± 0.011 | 14 |
| 28.2 ± 0.1 | 3.159 ± 0.011 | 13 |
| 28.9 ± 0.1 | 3.090 ± 0.010 | 5 |
| 29.0 ± 0.1 | 3.074 ± 0.010 | 3 |
| 29.6 ± 0.1 | 3.020 ± 0.010 | 8 |

*FIG. 2*

Raman peak list for crystalline (2S,3R,4R,5S,6R)-2-(4-chloro-3-(4-(2-cyclopropoxyethoxy)benzyl)phenyl)-6-(hydroxymethyl)tetrahydro-2*H*-pyran-3,4,5-triol (cm$^{-1}$)

| | |
|---|---|
| 144 | 1205 |
| 189 | 1212 |
| 216 | 1229 |
| 226 | 1302 |
| 284 | 1323 |
| 315 | 1343 |
| 353 | 1380 |
| 387 | 1422 |
| 419 | 1438 |
| 432 | 1457 |
| 449 | 1572 |
| 503 | 1585 |
| 530 | 1608 |
| 565 | 2844 |
| 594 | 2919 |
| 638 | 2945 |
| 688 | 2963 |
| 716 | 2997 |
| 728 | 3010 |
| 755 | 3028 |
| 790 | 3051 |
| 825 | 3063 |
| 850 | 3085 |
| 884 | 3095 |
| 901 | |
| 919 | |
| 934 | |
| 974 | |
| 984 | |
| 1014 | |
| 1030 | |
| 1052 | |
| 1070 | |
| 1120 | |
| 1134 | |
| 1178 | |

*FIG. 4*

| Family and Space Group | Monoclinic P2$_1$ (#4) |
| --- | --- |
| Z'/Z | 1/2 |
| a (Å) | 7.960 |
| b (Å) | 8.860 |
| c (Å) | 16.560 |
| α (deg) | 90 |
| β (deg) | 95.71 |
| γ (deg) | 90 |
| Volume (Å$^3$/cell) | 1162.1 |
| V/Z (Å$^3$/asym. Unit) | 581.1 |
| Assumed Composition[a] | C$_{24}$H$_{29}$O$_7$Cl |
| Density (g/cm$^3$)[a] | 1.329 |
| Weight Fraction Solvent (%)[a] | N/A |

[a]Density and weight fraction solvent are based on the assumed composition.

*FIG. 7*

CRYSTALLINE FORM OF BENZYLBENZENE SGLT2 INHIBITOR

CROSS-REFERENCE TO RELATED APPLICATION

This application is a continuation of U.S. application Ser. No. 15/805,074, filed Nov. 6, 2017, which is divisional of U.S. application Ser. No. 14/627,693 filed Feb. 20, 2015 (now U.S. Pat. No. 9,834,573), which is a divisional of U.S. application Ser. No. 13/158,724, filed Jun. 13, 2011 (now U.S. Pat. No. 8,987,323), which claims foreign priority under 35 U.S.C. § 119 to PCT/CN2010/073865, filed Jun. 12, 2010, each of which is incorporated in its entirety herein for all purposes.

BACKGROUND OF THE INVENTION

The sodium-dependent ("active") glucose cotransporters (SGLTs), including SGLT1 (found predominantly in the intestinal brush border) and SGLT2 (localized in the renal proximal tubule), have been significantly evaluated. In particular, SGLT2 has been found to be responsible for the majority of glucose reuptake by the kidneys. Inhibition of renal SGLT is now considered a useful approach to treating hyperglycemia by increasing the amount of glucose excreted in the urine (Arakawa K, et al., *Br J Pharmacol* 132:578-86, 2001; Oku A, et al., *Diabetes* 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., *J Am Soc Nephrol* 14:2873-82, 2003). Therefore, compounds which inhibit SGLT, particularly SGLT2, are promising candidates for use as antidiabetic drugs (reviewed in Washburn W N, *Expert Opin Ther Patents* 19:1485-99, 2009). In addition, since cancer cells show increased glucose uptake in comparison to their normal counterparts, SGLT inhibition has been proposed as a method for treating cancer by starving cancer cells. For example, studies suggest that SGLT2 plays a role in glucose uptake in metastatic lesions of lung cancer (Ishikawa N, et al., *Jpn J Cancer Res* 92:874-9, 2001). Thus, SGLT2 inhibitors may also be useful as anticancer agents.

In addition to pharmaceutical activity, a further consideration for the successful development of a medicament is the parameters which are connected with the physical nature of the active substance itself. Some of these parameters are stability of the active substance under various environmental conditions, stability of the active substance during production of the pharmaceutical formulation and the stability of the active substance in the final medicament compositions. In order to provide the necessary stability, the pharmaceutically active substance used in the medicament should be as pure as possible, leading to its stability in long-term storage under various environmental conditions.

Another factor to be considered is the uniform distribution of the active substance in the formulation, particularly when the active substance is to be given in low doses. To ensure uniform distribution, the particle size of the active substance can be reduced to a suitable level, e.g. by grinding. However, breakdown of the pharmaceutically active substance as a side effect of the grinding (or micronising) must be avoided. As a result, in view of the hard conditions required during the process, the active substance must be stable throughout the grinding process. Still further, if the active substance is not stable during the grinding process, a homogeneous pharmaceutical formulation with the specified amount of active substance is unlikely to be achieved in a reproducible manner.

Still another consideration associated with the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

Another consideration for the pharmaceutically active substance is stability in a formulation, which in turn gives rise to a longer shelf life of the particular medicament. In this instance, the shelf life is the length of time during which the medicament can be administered without any risk that the active substance has degraded. High stability of a medicament in the abovementioned pharmaceutical compositions under various storage conditions is therefore an additional advantage for both the patient and the manufacturer.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

The compound of the present invention has been prepared according to the methods of U.S. Publication No. 2009/0118201, filed Aug. 22, 2008, U.S. application Ser. No. 12/545,400, and PCT/US2009/054585, now WO2010/022313, both filed Aug. 21, 2009. The aim of the present invention is to provide a stable crystalline form of the compound which meets important requirements imposed on pharmaceutically active substances as mentioned above.

BRIEF SUMMARY OF THE INVENTION

The present invention provides crystalline forms of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol having an inhibitory effect on sodium-dependent glucose cotransporter 2 (SGLT2). The invention also provides pharmaceutical compositions, methods of preparing the crystalline form of the compound, and methods of using the compound, independently or in combination with other therapeutic agents, for treating diseases and conditions which are affected by SGLT2 inhibition.

BRIEF DESCRIPTION OF THE DRAWINGS

FIG. 2 provides a Table of XRPD data for the XRPD spectra in FIG. 1.

FIG. 4 provides a Raman peak list for the Raman spectra in FIG. 3.

FIG. 7 provides a table of unit cell data for crystalline (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol.

DETAILED DESCRIPTION OF THE INVENTION

I. Definitions

Figure 1:
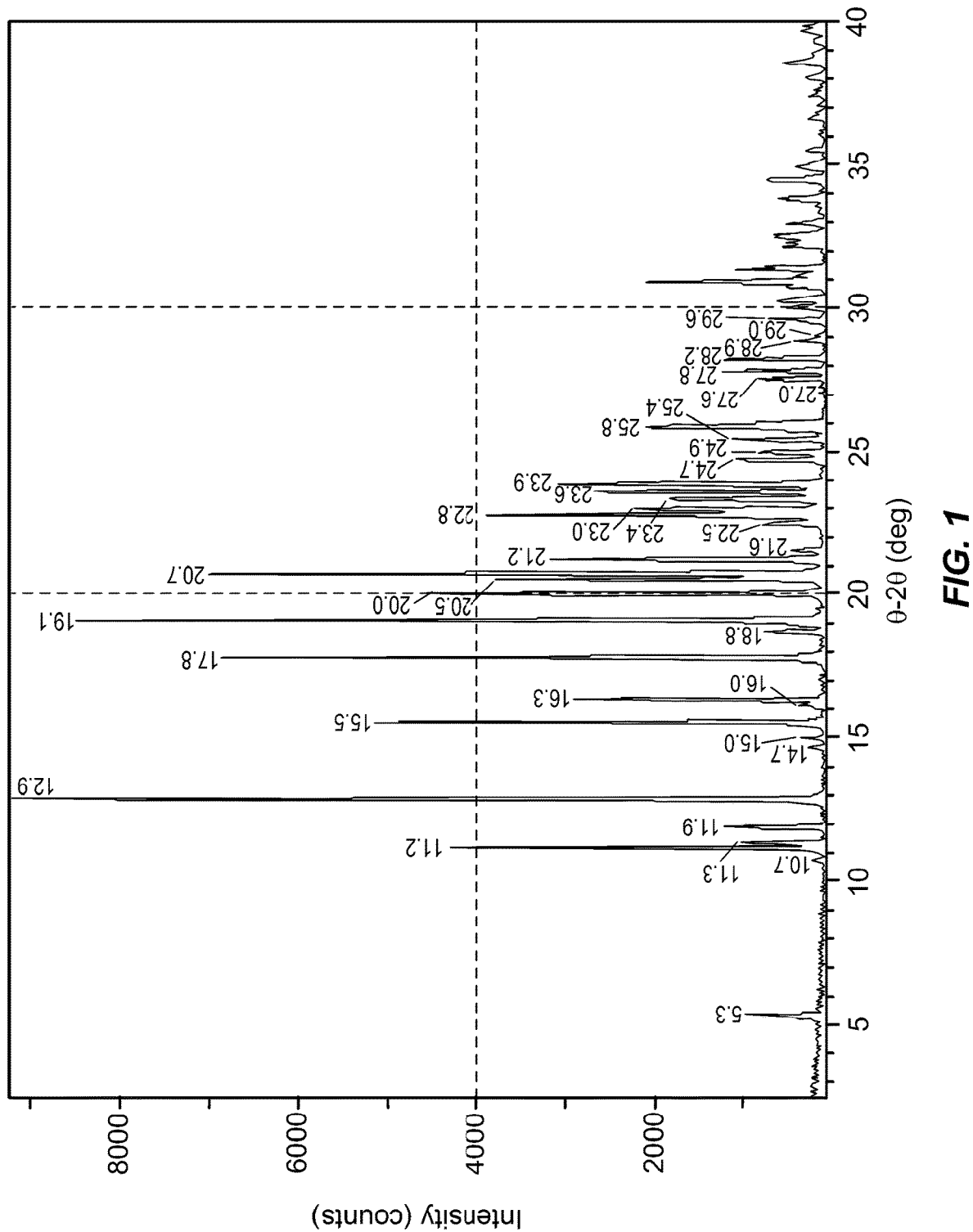
FIG. 1 provides the X-ray powder diffraction (XRPD) spectra of crystalline (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol.

As used herein, the terms "treating" and "treatment" refer to delaying the onset of, retarding or reversing the progress of, or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity.

As used herein, the term "compound" refers to a molecule produced by any means including, without limitation, synthesis in vitro or generation in situ or in vivo.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in Remington: The Science and Practice of Pharmacy, 21st Ed., Gennaro, Ed., Lippencott Williams & Wilkins (2003). As discussed therein, immediate and nonimmediate release can be defined kinetically by reference to the following equation:

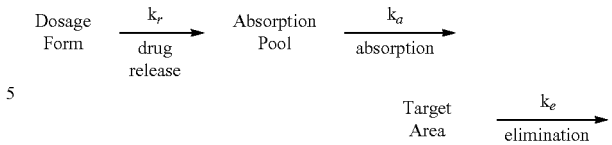

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

As used herein, the term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

II. Crystalline Forms

The present invention provides a crystalline form of a compound having an inhibitory effect on sodium-dependent glucose cotransporter SGLT, preferably SGLT2. Therefore, the crystalline compound of the present invention is suitable for the prevention and treatment of diseases and conditions, particularly metabolic disorders, including but not limited to type 1 and type 2 diabetes mellitus, hyperglycemia, diabetic complications (such as retinopathy, nephropathy, e.g., progressive renal disease, neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The present invention also provides pharmaceutical compositions and prodrugs of the crystalline form according to the present invention.

The present invention further provides synthetic processes for preparing the crystalline compound of the present invention.

The present invention also provides methods of using the crystalline form of the compound according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

In one aspect, the present invention provides a crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol. The chemical structure is shown below:

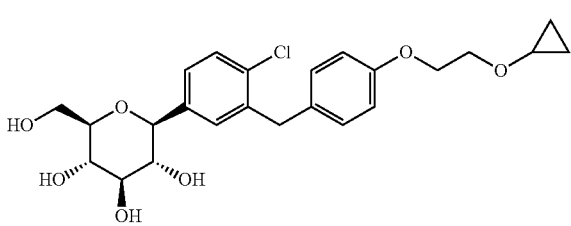

The crystalline compound of the present invention can be characterized by the X-ray powder diffraction (XRPD), the Raman spectra, the differential scanning calorimetry (DSC) endotherm, the thermal gravimetric analysis (TGA) showing decomposition temperature, and the unit cell of the crystal structure.

In some embodiments, the present invention provides the crystalline form of the compound characterized by the XRPD substantially in accordance with that of FIG. 1 and the peaks substantially in accordance with FIG. 2. The crystalline compound of the present invention can have any combination of peaks substantially in accordance with FIG. 2. Moreover, each peak listed in FIG. 2 can have an error range of ±0.2 degrees 2θ, preferably ±0.1 degrees 2θ.

In other embodiments, the crystalline form of the compound is characterized by an X-ray powder diffraction pattern that includes one or more peaks at 5.4, 11.2, 11.3, 11.9, 12.9, 15.5, 16.3, 17.8, 19.1, 20.0, 20.6, 20.7, 21.2, 22.8, 23.0, 23.4, 23.6, 23.9, 24.7, 25.4, 25.8, 27.8 and 28.2 degrees 2θ (±0.1 degrees 2θ), wherein said XRPD is made using CuK$_{α1}$ radiation. In another embodiment, the crystalline form of the compound is characterized by an XRPD that includes two or more, three or more, four or more, or five or more peaks at 5.4, 11.2, 11.3, 11.9, 12.9, 15.5, 16.3, 17.8, 19.1, 20.0, 20.6, 20.7, 21.2, 22.8, 23.0, 23.4, 23.6, 23.9, 24.7, 25.4, 25.8, 27.8 and 28.2 degrees 2θ (±0.1 degrees 2θ). In some other embodiments, the crystalline form of the compound is characterized by an XRPD that includes peaks at 12.9, 19.1 and 20.7 degrees 2θ (±0.1 degrees 2θ). In still other embodiments, the crystalline form of the compound is characterized by an XRPD that includes peaks at 11.2, 12.9, 15.5, 17.8, 19.1, 20.0 and 20.7 degrees 2θ (±0.1 degrees 2θ).

In yet other embodiments, the crystalline form of the compound is characterized by an XRPD that includes peaks at 5.4, 11.2, 11.9, 12.9, 15.5, 16.3, 17.8, and 19.1 degrees 2θ (±0.1 degrees 2θ). In still yet other embodiments, the crystalline form of the compound is characterized by an XRPD that includes peaks at 5.4, 11.2, 11.9, and 12.9 degrees 2θ (±0.1 degrees 2θ). In another embodiment, the crystalline form of the compound is characterized by an XRPD including peaks at 11.2 and 12.9 degrees 2θ (±0.1 degrees 2θ). In other embodiments, the crystalline form of the compound is characterized by the XRPD peaks substantially in accordance with FIG. 2.

Figure 3:
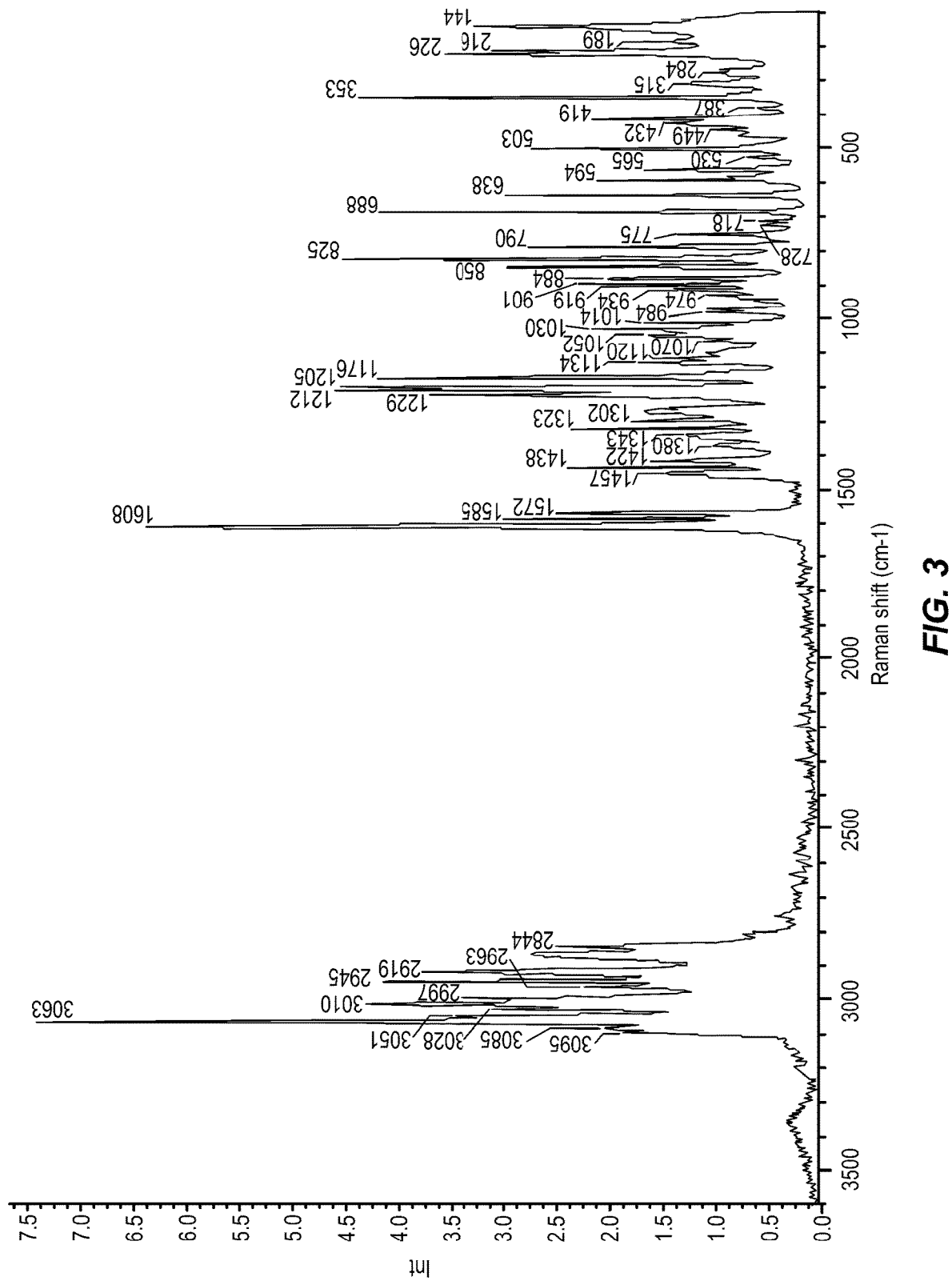
FIG. 3 provides the Raman spectra of crystalline (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol.

The crystalline compound of the present invention is also characterized by the Raman spectra substantially in accordance with FIG. 3 and the peaks substantially in accordance with FIG. 4. In some embodiments, the crystalline form of the compound is characterized by a Raman spectra that includes one or more peaks at about 353, 688, 825, 1178, 1205, 1212, 1608, 2945, 3010 and 3063 cm$^{-1}$. In another embodiment, the crystalline form of the compound is characterized by a Raman spectra that includes two or more, three or more, four or more, or five or more peaks. In other embodiments, the crystalline form of the compound is characterized by the Raman spectra including peaks at about 353, 688 and 825 cm$^{-1}$. In some other embodiments, the crystalline form of the compound is characterized by the Raman peaks substantially in accordance with FIG. 4.

The crystalline compound of the present invention is also characterized by the differential scanning calorimetry (DSC) endotherm. In some embodiments, the crystalline form of the compound is characterized by a DSC endotherm at about 136° C.

Figure 5:
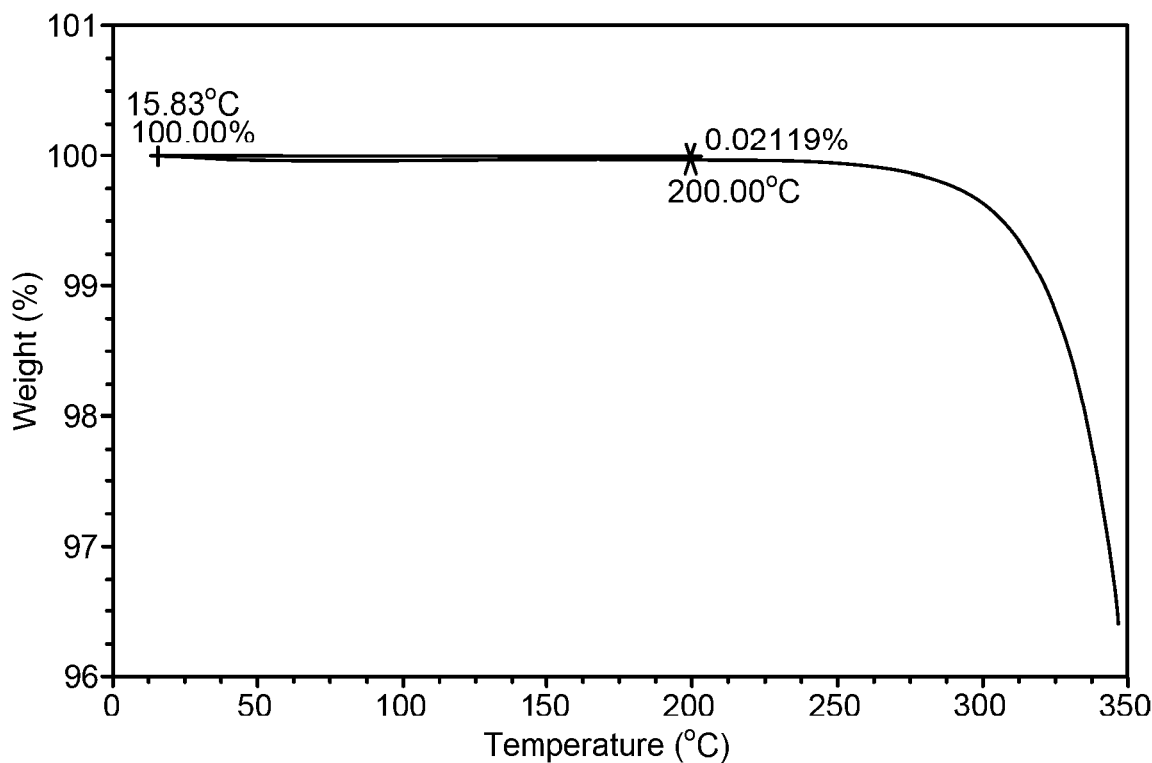
FIG. 5 provides the thermal gravimetric analysis (TGA) of crystalline (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol.
Figure 6:
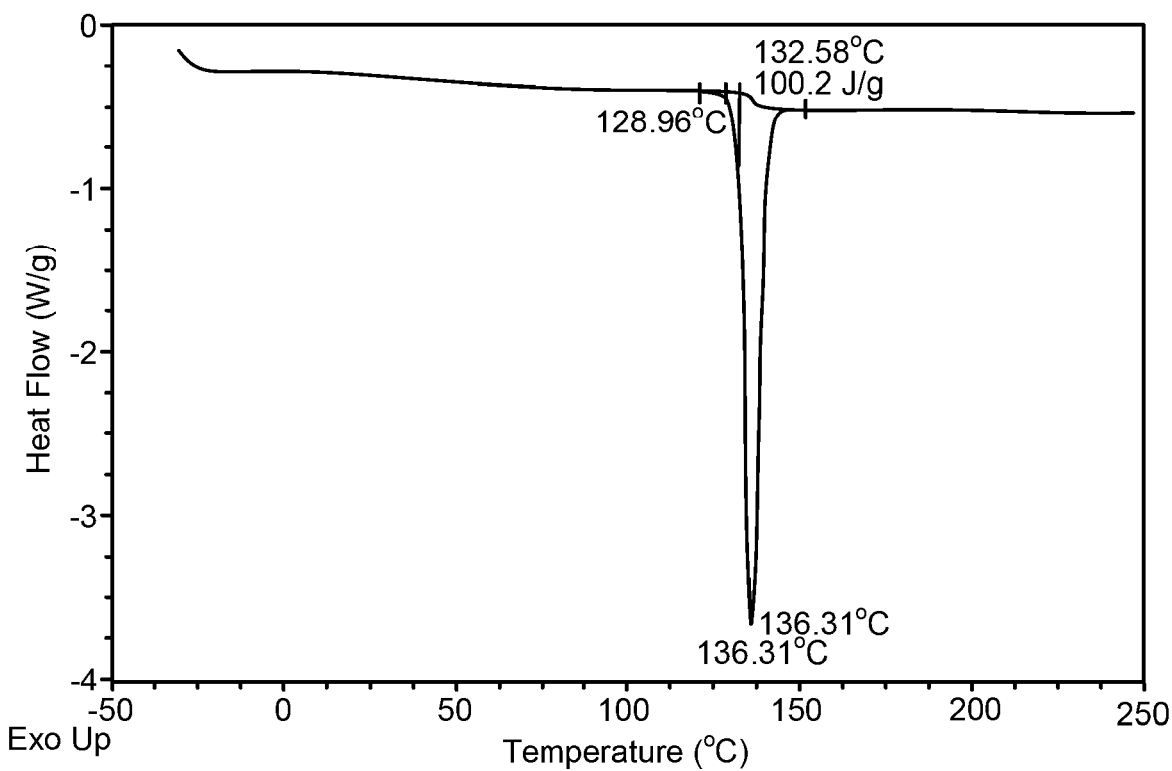
FIG. 6 provides the differential scanning calorimetry (DSC) spectra of crystalline (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol.

The crystalline compound of the present invention is also characterized by the unit cell data substantially in accordance with FIG. 7. Thermal gravimetric analysis (TGA) can also be used to characterize the crystalline compound of the present invention. For example, a representative TGA is substantially in accordance with that shown in FIG. 5, demonstrating thermal stability of the crystalline compound above 200° C.

In some embodiments, the crystalline compound is characterized by at least one of the following: at least one XRPD peak as described above, at least one Raman peak as described above, a DSC endotherm as described above, TGA data regarding thermal stability as described above, and unit cell data as described above and in FIG. 7. In other embodiments, the crystalline compound is characterized by at least two of the following: at least one XRPD peak as described above, at least one Raman peak as described above, a DSC endotherm as described above, TGA data regarding thermal stability as described above, and unit cell data as described above and in FIG. 7. For example, the crystalline compound can be characterized by at least one XRPD peak and at least one Raman peak, or at least one XRPD peak and the DSC endotherm, or at least one Raman peak and the DSC endotherm, or at least one XRPD peak and the unit cell data, or at least one Raman peak and the unit cell data, etc.

In some embodiments, the crystalline compound of the present invention is characterized by an X-ray powder diffraction (XRPD) pattern that includes one or more peaks at 5.4, 11.2, 11.3, 11.9, 12.9, 15.5, 16.3, 17.8, 19.1, 20.0, 20.6, 20.7, 21.2, 22.8, 23.0, 23.4, 23.6, 23.9, 24.7, 25.4, 25.8, 27.8 and 28.2 degrees 2θ (±0.1 degrees 2θ), wherein said XRPD is made using CuK$_{α1}$ radiation, and a Raman spectra that includes one or more peaks at about 353, 688, 825, 1178, 1205, 1212, 1608, 2945, 3010 and 3063 cm$^{-1}$. In other embodiments, the crystalline compound of the present invention is characterized by an X-ray powder diffraction (XRPD) pattern that includes one or more peaks at 11.2, 12.9, 15.5, 17.8, 19.1, 20.0, 20.6, 20.7, 21.2 and 22.8 and 28.2 degrees 2θ (±0.1 degrees 2θ), wherein said XRPD is made using CuK$_{α1}$ radiation, and a Raman spectra that includes one or more peaks at about 353, 688, and 825 cm$^{-1}$. In some other embodiments, the crystalline compound of the present invention is characterized by an X-ray powder diffraction (XRPD) pattern that includes one or more peaks at 11.2 and 12.9 degrees 2θ (±0.1 degrees 2θ), wherein said XRPD is made using CuK$_{α1}$ radiation, and a Raman spectra that includes one or more peaks at about 353, 688, and 825 cm$^{-1}$.

In other embodiments, the present invention provides a compound (2 S,3R,4R,5 S,6R)-2-(4-chloro-3-(4-(2-cyclopropoxyethoxy)benzyl)phenyl)-6-(hydroxymethyl)tetrahydro-2H-pyran-3,4,5-triol in crystalline form.

The present invention also includes isotopically-labeled forms of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds and prodrugs thereof, as well as isotopically-labeled, pharmaceutically acceptable salts and prodrugs thereof, are within the scope of the present invention. Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

III. Methods of Making Crystalline Form

Figure 8:
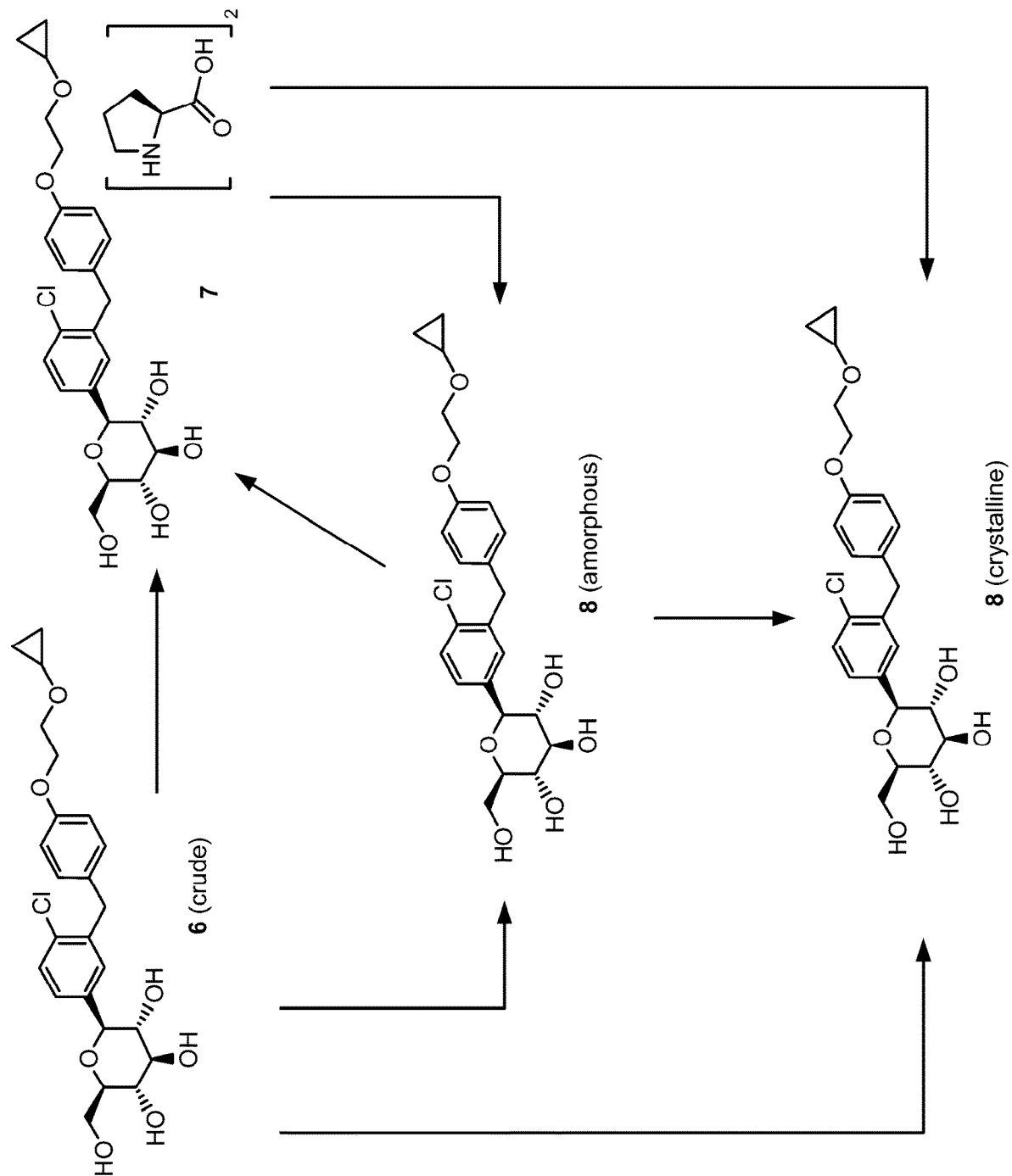
FIG. 8 provides a scheme for the preparation of crystalline (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol.

The crystalline form of the present invention can be obtained by a variety of methods, as outlined in FIG. 8. For example, the crystalline compound 8 can be prepared directly from L-proline complex 7. Alternatively, the L-proline of L-proline complex 7 can be removed to afford amorphous 8, which is then crystallized to crystalline 8. Crystalline 8 can also be prepared directly from crude compound 6, by first isolating and then crystallizing amorphous 8 to form crystalline 8, or directly from crude 6.

Other methods of preparing crystalline 8 are know to one of skill in the art. Moreover, each crystallization process can be repeated to remove additional impurities. In some embodiments, more than one of the various crystallization processes can be used to prepare the crystalline compound of the present invention.

In some embodiments, crystalline 8 can be prepared from the bis L-proline co-crystal of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol as described in the Examples. Briefly, the co-crystal starting materials is taken up in a suitable solvent (e.g., methanol or ethanol) to obtain a solution, and a precipitating solvent (e.g., water) is added to achieve crystallization of the desired compound.

Accordingly, the present invention further provides a method for making a crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, the method including (a) combining (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol bis(L-proline) complex and a suitable solvent with mixing to form a solution; (b) adding a precipitating solvent to the solution to provide a mixture; and (c) isolating the crystalline form from the mixture of step (b).

In some embodiments, the present invention provides a method for making a crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, the method including (a) combining (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol and a suitable solvent with mixing to form a solution; (b) adding a precipitating solvent to the solution to provide a mixture; and (c) isolating the crystalline form from the mixture of step (b).

In other embodiments, the present invention provides a method for making a crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, the method including (a) combining amorphous (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol and a suitable solvent with mixing to form a solution; (b) adding a precipitating solvent to the solution to provide a mixture; and (c) isolating the crystalline form from the mixture of step (b).

In step (a) of the above methods, the solvent can be any solvent suitable to form a solution, and which is miscible with the precipitating solvent used in step (b). Typically the solvent in step (a) is a polar solvent, which in some embodiments is a protic solvent. Suitable solvents include, $C_1$-$C_4$ alcohols, ethylene glycol and polyethylene glycol such as PEG400, alkanoates such as ethyl acetate, isopropyl acetate, propyl acetate, and butyl acetate, acetonitrile, alkanones such as acetone, butanone, methyl ethyl ketone and methyl propyl ketone, and mixtures of two or more of these solvents. More preferred solvents are selected from the group consisting of methanol, ethanol, isopropanol, ethyl acetate, acetone, and mixture of two or more of these solvents. Still further preferred are methanol and ethanol. In one selected embodiment, the solvent used in step (a) is methanol.

Step (a) of the above methods can be carried out at temperatures generally from about 0° C. to the reflux temperature of the solvent (e.g., 65° C. for methanol). A preferred temperature range is between about 35° C. and 100° C., even more preferably from about 45° C. to 80° C. Once a solution is obtained, a precipitating solvent is added. A precipitating solvent is one in which the product is much less soluble than the initial solution solvent. Suitable precipitating solvents include water, ethers, cyclic ethers, alkanes, cycloalkanes, phenyls and mixtures thereof, in particular $C_4$-$C_6$-aliphatic ethers, $C_6$-$C_8$-alkanes, $C_6$-$C_8$-cycloalkanes, phenyls such as benzene, toluene and xylene, and mixtures thereof. Examples of precipitating solvents are diisopropylether, tert-butylmethylether (TBME), cyclohexane, methylcyclohexane, hexane, heptane, octane and mixtures thereof. In one selected embodiment, the precipitating solvent is water.

The precise ratios of solvents and starting material are less critical to the invention, but optimized ratios can produce greater yields and more uniform crystallized product. The ratio of solvents in the above methods can be any suitable ratio from about 1:1 to about 1:9, including about 1:2, 1:3, 1:4, 1:5, 1:6, 1:7 and about 1:8. The range of solvent ratios is preferably from about 1:1 to about 1:9, more preferably from about 1:2 to about 1:7, even more preferably from about 1:2 to about 1:5. In one group of embodiments, when methanol is used as solvent and water is the precipitating solvent, the ratio of methanol to water in the mixture of step (b) is from about 1:1 to about 1:9 by volume, more preferably about 1:5 by volume.

The ratio of complex to solvent, such as a methanol and water mixture, can be any suitable ratio to promote crystallization. For example, the complex to solvent ratio can be from about 1:5 (weight/volume, or w/v) to about 1:50 (w/v), including about 1:6, 1:7, 1:8, 1:9, 1:10, 1:11, 1:12, 1:13, 1:14, 1:15, 1:20, 1:25, 1:30, 1:35, 1:40 and about 1:45 (w/v). The complex to solvent ratio is preferably from about 1:10 to about 1:25 (w/v), more preferably from about 1:10 to about 1:15 (w/v). In another group of embodiments, the ratio of complex to solvent and precipitating solvent in the mixture of step (b) is from about 1:10 to about 1:25 (w/v). In other embodiments, the ratio of complex to methanol and water in the mixture of step (b) is from about 1:10 to about 1:25 (w/v). In some other embodiments, the ratio of complex to methanol and water in the mixture of step (b) is from about 1:2:7 (w/v/v) to about 1:3:10 (w/v/v), preferably about 1:2:10 (w/v/v).

The mixture for crystallizing crystalline 8 can also contain a variety of other components, such as acids, bases and salts. Acids useful in the present invention include, but are not limited to, acetic acid, formic acid, hydrochloric acid, sulfuric acid, and other weak acids and strong acids. Bases useful in the present invention include, but are not limited to, ammonia, sodium hydroxide, and others. Salts useful in the present invention include, but are not limited to, sodium chloride, potassium chloride, potassium carbonate and others. In some embodiments, the mixture of step (b) in the above methods includes sodium hydroxide. In other embodiments, the mixture of step (b) in the above methods includes sodium chloride.

After addition of the precipitating solvent, the mixture is generally kept at room temperature, or cooled, for a sufficient period of time to allow complete crystal formation of the product to occur. The temperature of the mixture in step (b) is preferably about the same as or lower than in step (a). During storage the temperature of the solution containing the product is preferably lowered to a temperature in the range from −10° C. to 25° C. or even lower, even more preferably in the range from −5° C. to 15° C. Step (b) can be carried out with or without stirring. As noted above, the conditions for step (b) can affect the size, shape and quality of the obtained crystals.

Crystallization can be induced by methods known in the art, for example by mechanical means such as scratching or rubbing the contact surface of the reaction vessel with e.g. a glass rod. Optionally the saturated or supersaturated solution may be inoculated with seed crystals. The mixture for crystallizing crystalline 8 can also contain a seed crystal of crystalline compound 8. In some embodiments, the solution or mixture in the above methods includes a seed crystal of the crystalline compound of the present invention.

Isolation of the desired crystalline form can be accomplished by removing the solvent and precipitating solvent from the crystals. Generally this is carried out by known methods as for example filtration, suction filtration, decantation or centrifugation. Further isolation can be achieved by removing any excess of the solvent(s) from the crystalline form by methods known to the one skilled in the art as for example application of a vacuum, and/or by heating above 20° C., preferably in a temperature range below 80° C., even more preferably below 50° C.

In other embodiments, the present invention provides a method for making a crystalline form of (2 S,3R,4R,5 S,6R)-2-(4-chloro-3-(4-(2-cyclopropoxyethoxy)benzyl) phenyl)-6-(hydroxymethyl)tetrahydro-2H-pyran-3,4,5-triol, the method including (a) combining (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol and a suitable solvent with mixing to form a solution; and (b) isolating the crystalline form from the solution. In other embodiments, the method also includes adding a precipitating solvent to the solution. In step (a) of the above methods, the solvent can be any solvent suitable to form a solution. Suitable solvents include alkanoates such as ethyl acetate, isopropyl acetate, propyl acetate, and butyl acetate, ethers such as ethyl ether, methyl tert-butyl ether and mixtures of two or more of these solvents. More preferred solvents are selected from the group consisting of ethyl acetate, ethyl ether, methyl tert-butyl ether and mixture of two or more of these solvents. Still further preferred are ethyl acetate and methyl tert-butyl ether. The (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol can have any suitable form, including amorphous, crystalline, or a combination thereof. Moreover, the (2S,3R,4R,5S,6R)-2-(4-chloro-3-(4-(2-cyclopropoxyethoxy)benzyl)phenyl)-6-(hydroxymethyl) tetrahydro-2H-pyran-3,4,5-triol can have any suitable level of purity, such as purified or unpurified.

In some embodiments, the (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol is amorphous (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol. The amorphous (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, amorphous compound 8, can be prepared by a variety of methods known in the art. For example, the amorphous compound 8 can be isolated from crude mixture 6 using known methods of isolating. Alternatively, amorphous compound 8 can be prepared from complex 7 by removing the L-proline using methods known in the art. In some embodiments, the amorphous (2S,3R,4R,5S,6R)-2-(4-chloro-3-(4-(2-cyclopropoxyethoxy)benzyl)phenyl)-6-(hydroxymethyl) tetrahydro-2H-pyran-3,4,5-triol is prepared from (2S,3R,4R, 5S,6R)-2-(4-chloro-3-(4-(2-cyclopropoxyethoxy)benzyl) phenyl)-6-(hydroxymethyl)tetrahydro-2H-pyran-3,4,5-triol bis(L-proline) by combining (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol bis(L-proline) complex and a suitable solvent mixture with mixing to form a solution, and isolating amorphous (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol from the solution. Suitable solvents and solvent mixtures are described above.

IV. Pharmaceutical Compositions

The present invention further provides a pharmaceutical composition comprising an effective amount of a crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, in a pharmaceutically acceptable excipient.

The crystalline form provided in this invention can be incorporated into a variety of formulations for therapeutic administration. More particularly, the crystalline form of the present invention can be formulated into pharmaceutical compositions, by formulation with appropriate pharmaceutically acceptable excipients or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the crystalline form of the present invention can be achieved in various ways, including oral, buccal, parenteral, intravenous, intradermal (e.g., subcutaneous, intramuscular), transdermal, etc., administration. Moreover, the crystalline form can be administered in a local rather than systemic manner, for example, in a depot or sustained release formulation.

Suitable formulations for use in the present invention are found in *Remington: The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, the crystalline form of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, the crystalline form of the present invention can be formulated readily by combining with pharmaceutically acceptable excipients that are well known in the art. Such excipients enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The crystalline forms described herein can also be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, the crystalline forms of the invention can be formulated in aqueous solutions, preferably in physiologically compatible buffers such as Hank's solution, Ringer's solution, or physiological saline buffer. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in conventional manner.

In addition to the formulations described previously, a crystalline form of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the crystalline forms of the invention in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

V. Methods of Use

The present invention further provides methods of using the crystalline forms of (2S,3R,4R,5S,6R)-2-(4-chloro-3-(4-(2-cyclopropoxyethoxy)benzyl)phenyl)-6-(hydroxymethyl) tetrahydro-2H-pyran-3,4,5-triol for the prevention and treatment of disease. In one embodiment, the present invention provides a method of treating a disease or condition affected by inhibiting SGLT2, the method including administering to a subject in need thereof a therapeutically effective amount of a composition comprising a crystalline form of the compound of the present invention. Diseases affected by inhibiting SGLT2 include, but are not limited to, type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis, cancer and related diseases, which comprises administering an effective amount of (2S,3R,4R,5S,6R)-2-(4-chloro-3-(4-(2-cyclopropoxyethoxy)benzyl)phenyl)-6-(hydroxymethyl) tetrahydro-2H-pyran-3,4,5-triol, to a subject in need thereof. In another embodiment the invention provides a method of using the crystalline compound, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis, cancer and related diseases. In other embodiments, the invention provides a method of treating type 1 diabetes mellitus, type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis, and cancer.

In other embodiments, the present invention provides a method of treating diabetes, the method including administering to a subject in need thereof a therapeutically effective amount of a composition comprising a crystalline form of the compound of the present invention. The diabetes can be any suitable form of diabetes, including, but not limited to, type 1 diabetes mellitus, type 2 diabetes mellitus, and diabetic complications. In some embodiments, the diabetes is type 1 diabetes mellitus. In some other embodiments, the diabetes is type 2 diabetes mellitus.

The present invention also contemplates the use of the crystalline forms of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with crystalline forms of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol of the present invention include insulin and insulin mimetics, sulfonylureas (such as acetohexamide, carbutamide, chlorpropamide, glibenclamide, glibornuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid-x receptor (RXR) agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, alogliptin, dutogliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), glucokinase activators (such as ARRY-403, piragliatin (R04389620), R00281675, MK-0941, TTP355, GKA50, GKA60, GKM-001, PSN010, PSN-GK1, compounds described in Sarabu, R., et al., Expert Opinion on Therapeutic Patents, Vol. 21, No. 1, 2011, pp. 13-33, and the like), protein tyrosine phosphatase-1B inhibitors (such as KR61639, IDD-3, PTP-3848, PTP-112, OC-86839, PNU-177496, compounds described in Vats, R. K., et al., Current Science, Vol. 88, No. 2, 25 Jan. 2005, pp. 241-249, and the like), glycogen phosphorylase inhibitors (such as NN-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., Current Science, Vol. 88, No. 2, 25 Jan. 2005, pp. 241-249, and the like), 11 beta-hydroxysteroid dehydrogenase type 1 inhibitors (such as carbenoxolone, INCB13739 and the like), glucagon receptor antagonists (such as BAY-27-9955, NN-2501, NNC-92-1687 and the like), glucagon-like peptide-1 (GLP-1), GLP-1 receptor agonists (such as exenatide, liraglutide, CJC-1131, AVE-0100, AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with the crystalline compound of the present invention include aldose reductase inhibitors (such as epalrestat, imirestat, tolrestat, minalrestat, ponalrestat, zopolrestat, fidarestat, ascorbyl gamolenate, ADN-138, BAL-ARI8, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation end-products (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with the crystalline compound of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with the crystalline compound of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506, 219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, $C_1$-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-$C_8$-434, CI-976, RP-64477, F-1394, CS-505, CL-283546, YM-17E, 447$C_{88}$, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with the crystalline compound of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, aminepine and the like), serotonin-norepinephrine-dopamine reuptake inhibitors (such as tesofensine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as, 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, MK-212, BVT.933, YM-348, IL-639, IK-264, ATH-88651, ATHX-105 and the like (see, e.g., Nilsson B M, J. Med. Chem. 2006, 49:4023-4034)), beta-3 adrenergic receptor agonists (such as L-796568, CGP 12177, BRL-28410, SR-58611A, ICI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, A-71378, FPL-15849, GI-248573, GW-7178, GI-181771, GW-7854, GW-5823, and the like), antidepressant/acetylcholinesterase inhibitor combinations (such as venlafaxine/rivastigmine, sertraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB1 receptor antagonists (such as rimonabant, SR147778, SLV 319 and the like (see, e.g., Antel J et al., J. Med. Chem. 2006, 49:4008-4016)), melanin-concentrating hormone receptor antagonists (such as GlaxoSmithKline 803430X, GlaxoSmithKline 856464, SNAP-7941, T-226296 and the like (see, e.g., Handlon A L and Zhou H, J. Med. Chem. 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., J. Med. Chem. 2006, 49:4035-4043)), selective muscarinic receptor $M_1$ antagonists (such as telenzepine, pirenzepine and the like), opioid receptor antagonists (such as naltrexone, methylnaltrexone, nalmefene, naloxone, alvimopan, norbinaltorphimine, nalorphine and the like), and combinations thereof.

Examples of antihypertensive agents and agents for treating chronic heart failure, atherosclerosis or related diseases suitable for use in combination with the crystalline compound of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, barnidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and antiplatelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a crystalline form of (2S,3R,4R,5S,6R)-2-(4-chloro-3-(4-(2-cyclopropoxyethoxy)benzyl)phenyl)-6-(hydroxymethyl) tetrahydro-2H-pyran-3,4,5-triol, and at least one member selected from the group of therapeutic agents listed above as combination partners, in a pharmaceutically acceptable excipient.

The crystalline compound of the present invention is also useful for treatment of glucose disorders. In some embodiments, the present invention provides a method of decreasing blood glucose in a subject in need thereof, the method including administering to the subject an effective amount of a composition comprising a crystalline form of the compound of the present invention. In other embodiments, the present invention provides a method of lowering plasma levels of glycated hemoglobin (HbA1c) in a subject in need thereof, the method including administering to the subject an effective amount of a composition comprising a crystalline form of the compound of the present invention. In still other embodiments, the present invention provides a method of increasing the excretion of glucose in the urine of a subject in need thereof, said method comprising administering to the subject an effective amount of a composition comprising a crystalline form of the compound of the present invention.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, the crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Any conflict between any reference cited herein and the teaching of this specification is to be resolved in favor of the latter. Similarly, any conflict between an art-recognized definition of a word or phrase and a definition of the word or phrase as provided in this specification is to be resolved in favor of the latter. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

VI. Examples

The following examples are offered for illustrative purposes, and are not intended to limit the invention in any manner. Those of skill in the art will readily recognize a variety of noncritical parameters which can be changed or modified to yield essentially the same results.

The names of compounds shown in the following examples were derived from the structures shown using the CambridgeSoft Struct=Name algorithm as implemented in ChemDraw Ultra version 10.0. Unless otherwise indicated, the structures of compounds synthesized in the examples below were confirmed using the following procedures:

(1) Gas chromatography-mass spectra with electrospray ionization (MS ESI) were obtained with an Agilent 5973N mass spectrometer equipped with an Agilent 6890 gas chromatograph with an HP-5 MS column (0.25 µm coating; 30 m×0.25 mm). The ion source was maintained at 230° C. and spectra were scanned from 25-500 amu at 3.09 sec per scan.

(2) High pressure liquid chromatography mass spectra (LC-MS) were obtained using Finnigan Surveyor HPLC equipped with a quaternary pump, a variable wavelength detector set at 254 nm, an XB-C18 column (4.6×50 mm, 5 µm), and a Finnigan LCQ ion trap mass spectrometer with electrospray ionization. Spectra were scanned from 80-2000 amu using a variable ion time according to the number of ions in the source. The eluents were B: acetonitrile and D: water. Gradient elution from 10% to 90% B in 8 min at a flow rate of 1.0 mL/min is used with a final hold at 90% B of 7 min. Total run time is 15 min.

(3) Routine one-dimensional NMR spectroscopy was performed on 400 MHz or 300 MHz Varian Mercury-Plus spectrometers. The samples were dissolved in deuterated solvents obtained from Qingdao Tenglong Weibo Technology Co., Ltd., and transferred to 5 mm ID NMR tubes. The spectra were acquired at 293 K. The chemical shifts were recorded on the ppm scale and were referenced to the appropriate solvent signals, such as 2.49 ppm for DMSO-d6, 1.93 ppm for $CD_3CN$, 3.30 ppm for $CD_3OD$, 5.32 ppm for $CD_2Cl_2$ and 7.26 ppm for $CDCl_3$ for $^1H$ spectra.

When the following abbreviations and acronyms are used throughout the disclosure, they have the following meanings: ACN, acetonitrile; $Ac_2O$, acetic anhydride; AcOEt, ethyl acetate; AcOH, acetic acid; $AlBr_3$, aluminum bromide; $AlCl_3$, aluminum chloride; $BBr_3$, boron tribromide; $BF_3 \cdot Et_2O$, boron trifluoride etherate; n-BuLi, n-butyllithium; s-BuLi, s-butyllithium; t-BuLi, t-butyllithium; t-BuOK, potassium tert-butoxide; $CaCl_2$, calcium chloride; calc., calculated; $CD_3OD$, methanol-$d_4$; $CDCl_3$, chloroform-d; $CF_3SO_3H$, trifluoromethanesulfonic acid; $CH_2Cl_2$, methylene chloride; $CH_2I_2$, methylene iodide; $CH_3CN$, acetonitrile; $(COCl)_2$, oxalyl chloride; DAST, (diethylamino)sulfur trifluoride; DCM, dichloromethane; DIAD, diisopropyl azodicarboxylate; DMAP, 4-dimethylaminopyridine; DMEM, Dulbecco's Modified Eagle Medium; DMF, N,N-dimethylformamide; DMP, Dess-Martin periodinane; DMSO, dimethylsulfoxide; EA, ethyl acetate; eq, equivalents; ESI, electrospray ionization; Et, ethyl; $Et_3SiH$, triethylsilane; EtOAc, ethyl acetate; EtOH, ethanol; FBS, fetal bovine serum; h, hour; Hz, hydrogen gas; $H_2SO_4$, sulfuric acid; Hepes, 4-(2-hydroxyethyl)-1-piperazineethanesulfonic acid; $^1H$ NMR, proton nuclear magnetic resonance; HPLC, high performance liquid chromatography; IPA, isopropyl alcohol (2-propanol); IPC, In-Process Control; $K_2CO_3$, potassium carbonate; $K_2CrO_7$, potassium dichromate; KOH, potassium hydroxide; LC-ESI-MS, liquid chromatography electrospray ionization mass spectrometry; LC-MS, liquid chromatography-mass spectroscopy; Me, methyl; MeOH, methanol; $MeSO_3H$, methanesulfonic acid; Mg, magnesium; $MgCl_2$, magnesium chloride; min, minute; MS, mass spectroscopy; MsOH, methanesulfonic acid; NaH, sodium hydride; $NaHCO_3$, sodium bicarbonate; NaOAc, sodium acetate; NaOH, sodium hydroxide; $Na_2SO_4$, sodium sulfate; $NH_4Cl$, ammonium chloride; Pd/C, palladium on carbon; PE, petroleum ether; Ph, phenyl; $POCl_3$, phosphorus oxychloride; $PPh_3$, triphenylphosphine; Rf, retention factor; rt, room temperature; $SOCl_2$, thionyl chloride; TBAI, tetrabutylammonium iodide; TFA, trifluoroacetic acid; THF, tetrahydrofuran; TLC, thin layer chromatography; TMS, trimethylsilyl; Tris, trishydroxymethylaminomethane (or 2-amino-2-(hydroxymethyl)propane-1,3-diol).

Example 1. Preparation of (2S,3R,4R,5S,6R)-2-(4-chloro-3-(4-(2-cyclopropoxyethoxy) benzyl)phenyl)-6-(hydroxymethyl)tetrahydro-2H-pyran-3,4,5-triol, Bis(L-Proline) Complex

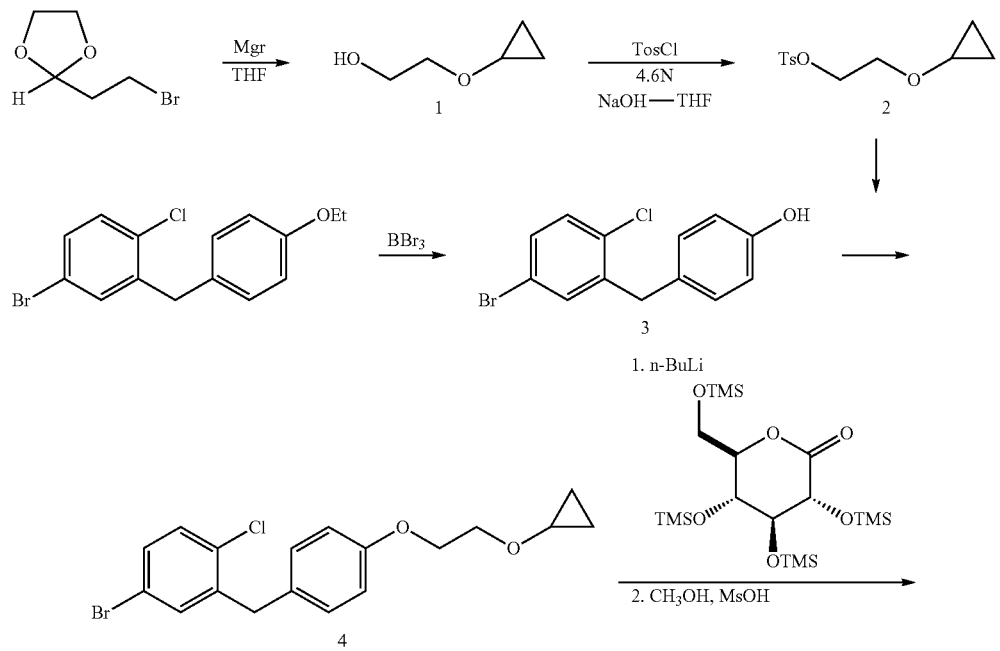

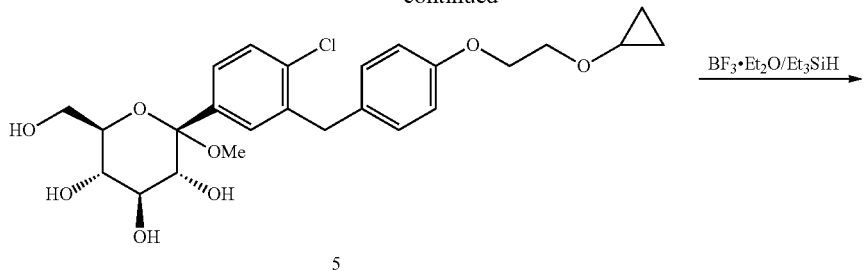

5

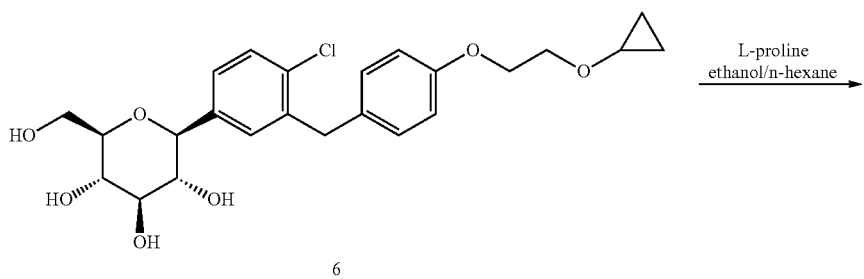

6

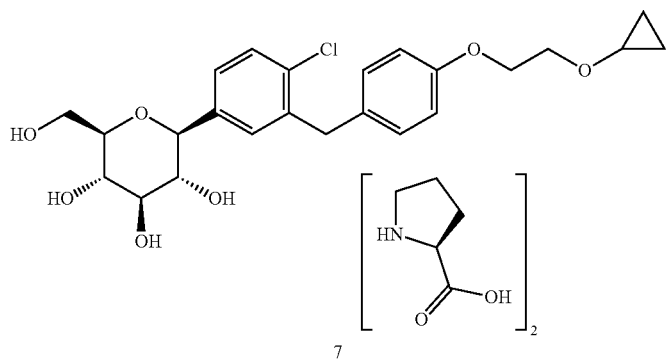

7

Example 1A

Preparation of 2-cyclopropoxyethanol (1)

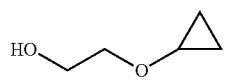

To a suspension of Mg powder (86.7 g, 3.6 mol) and iodine (cat) in anhydrous THF (0.7 L) was added slowly 1,2-dibromoethane (460 g, 2.4 mol) in anhydrous THF (2 L) slowly at a rate as to keep the internal temperature between 40-55° C. After the addition, a solution of 2-(2-bromoethyl)-1,3-dioxolane (100 g, 0.56 mol) in anhydrous THF (750 mL) was added dropwise. The reaction mixture was kept at 40-55° C. for 16h and was quenched by addition of aqueous solution of ammonium chloride. The mixture was extracted with methylene chloride. The organic layer was dried over sodium sulfate, and concentrated to give the title product (27 g) as yellow oil, which was directly used without further purification.

Example 1B

Preparation of 2-cyclopropoxyethyl 4-methylbenzenesulfonate (2)

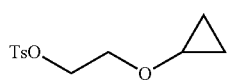 [SMILES: Cc1ccc(S(=O)(=O)OCCOC2CC2)cc1]

To a stirred solution of sodium hydroxide (32 g, 0.8 mol) in water (180 mL) and THF (180 mL) was added Example 1A (27 g, 0.26 mol) at −5 to 0° C. Afterwards, a solution of p-toluenesulfonyl chloride (52 g, 0.27 mol) in THF (360 mL) was added dropwise. The reaction mixture was kept at −5 to 0° C. for 16 h. The reaction mixture was then kept at room temperature for 30 min. The organic layer was separated and the aqueous layer was extracted with ethyl acetate (2×1.0 L). The combined organic layers were washed with brine, dried over Na$_2$SO$_4$ and concentrated to get the crude product as yellow oil (53.3 g). It was used directly without further purification.

Example 1C

Preparation of 4-(5-bromo-2-chlorobenzyl)phenol (3)

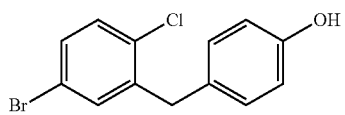 [SMILES: Oc1ccc(Cc2cc(Br)ccc2Cl)cc1]

To a stirred solution of 4-bromo-1-chloro-2-(4-ethoxybenzyl)benzene (747 g, 2.31 mol) in dichloromethane was added boron tribromide (1.15 kg, 4.62 mol) slowly at −78° C. The reaction mixture was allowed to rise to room temperature. When the reaction was complete as measure by TLC, the reaction was quenched with water. The mixture was extracted with dichloromethane. The organic layer was washed with aqueous solution of saturated sodium bicarbonate, water, brine, dried over $Na_2SO_4$, and concentrated. The residue was recrystallized in petroleum ether to give the title compound as a white solid (460 g, yield 68%). $^1$H NMR ($CDCl_3$, 400 MHz): δ 7.2~37.29 (m, 3H), 7.08 (d, J=8.8 Hz, 2H), 6.79 (d, J=8.8 Hz, 2H), 5.01 (s, 1H), 4.00 (s, 2H).

Example 1D

Preparation of 4-bromo-1-chloro-2-(4-(2-cyclopropoxyethoxy)benzyl)benzene (4)

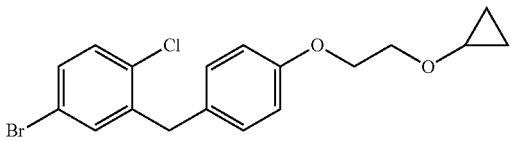 [SMILES: Clc1ccc(Br)cc1Cc1ccc(OCCOC2CC2)cc1]

A mixture of Example 1C (56.7 g, 210 mmol) and $Cs_2CO_3$ (135 g, 420 mmol) in DMF (350 mL) was stirred at room temperature for 0.5 h. Example 1B (53.3 g, 210 mmol) was added. The reaction mixture was stirred at room temperature overnight. It was diluted with water (3 L) and extracted with EtOAc. The organic layer was washed with water, brine, dried over $Na_2SO_4$, and concentrated. The residue was purified by flash column chromatography on silica gel eluting with petroleum ether:ethyl acetate (10:1) to give the title compound as liquid (51 g, yield 64%). $^1$H NMR ($CDCl_3$, 400 MHz): δ 7.2~27.29 (m, 3H), 7.08 (d, J=8.8 Hz, 2H), 6.88 (d, J=8.8 Hz, 2H), 4.10 (t, J=4.8 Hz, 2H), 3.86 (t, J=4.8 Hz, 2H), 3.38-3.32 (m, 1H), 0.62-0.66 (m, 2H), 0.49-0.52 (m, 2H).

Example 1E

Preparation of (2S,3R,4S,5S,6R)-2-(4-chloro-3-(4-(2-cyclopropoxyethoxy) benzyl)phenyl)-6-(hydroxymethyl)-2-methoxytetrahydro-2H-pyran-3,4,5-triol (5)

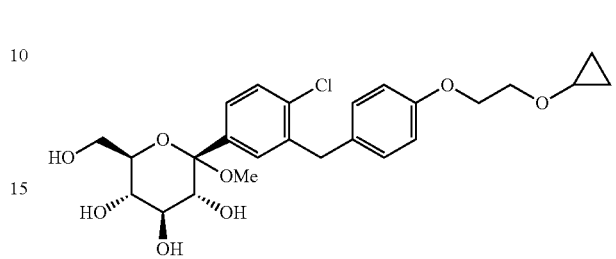

To a stirred solution of Example 1D (213 g) in anhydrous THF/toluene (1:2 (v/v), 1.7 L) under argon was added n-BuLi (2.5 M hexane, 245.9 mL) drop wise at −60±5° C. The mixture was stirred for 30 min. before transferred to a stirred solution of 2,3,4,6-tetra-O-trimethylsilyl-β-D-glucolactone (310.5 g) in toluene (1.6 L) at −60±5° C. The reaction mixture was continuously stirred at −60±5° C. for 1 h before quenching with aqueous solution of saturated ammonium chloride (1.5 L). Then mixture was allowed to warm to room temperature and stirred for 1 h. The organic layer was separated and the water layer was extracted with ethyl acetate (3×500 mL). The combined organic layers were washed with brine (1 L), dried over $Na_2SO_4$, and concentrated. The residue was dissolved in methanol (450 mL) and methanesulfonic acid (9.2 mL) was added at 0° C. The solution was allowed to warm to room temperature and stirred for 20 h. It was quenched with aqueous solution of sodium bicarbonate (50 g) in water (500 mL) and additional water (900 mL) was added. The mixture was extracted with ethyl acetate (3×1.0 L). The combined organic layers were washed with brine, dried over $Na_2SO_4$, concentrated and used directly in the next step without further purification.

Example 1F

Preparation of (2S,3R,4R,5S,6R)-2-(4-chloro-3-(4-(2-cyclopropoxyethoxy) benzyl)phenyl)-6-(hydroxymethyl)tetrahydro-2H-pyran-3,4,5-triol, Bis(L-Proline) Complex (7)

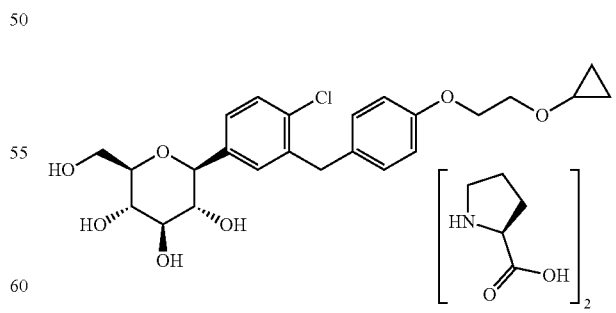

To stirred solution of Example 1E in $CH_2Cl_2/CH_3CN$ (650 mL:650 mL) at −5° C. was added triethylsilane (28.2 mL, 563 mmol), and followed by $BF_3·Et_2O$ (52.3 mL, 418.9 mmol). The reaction was stirred for 16 h while the temperature was allowed to warm to room temperature gradually.

The reaction was quenched with aqueous solution of saturated sodium bicarbonate to pH 8.0. The organic volatiles were removed under vacuum. The residue was partitioned between ethyl acetate (2.25 L) and water (2.25 L). The organic layer was separated, washed with brine, dried over Na$_2$SO$_4$ and concentrated to give the crude product 6 (230 g, purity 82.3%). This product and L-proline (113.7 g) in EtOH/H$_2$O (15:1 v/v, 2.09 L) was stirred at 80° C. for 1 h when it became a clear solution. Hexane (3.0 L) was added dropwise into the above hot solution over 50 min, with the temperature being kept at about 60° C. The reaction mixture was stirred overnight at room temperature. The solid was filtered and washed with EtOH/H$_2$O (15:1 (v/v), 2×300 mL), hexane (2×900 mL), and dried at 45° C. under vacuum for 10 h to give the pure title compound 7 as a white solid (209 g). Purity (HPLC) 99.2% (UV). $^1$H NMR (CD$_3$OD, 400 MHz): δ 7.25~7.34 (m, 3H), 7.11 (d, J=8.8 Hz, 2H), 6.84 (d, J=8.8 Hz, 2H), 4.03-4.11 (m, 5H), 3.96-4.00 (m, 2H), 3.83-3.90 (m, 3H), 3.68-3.72 (m, 1H), 3.36-3.46 (m, 6H), 3.21-3.30 (m, 3H), 2.26-2.34 (m, 2H), 2.08-2.17 (m, 2H), 1.94-2.02 (m, 4H), 0.56-0.57 (m, 2H), 0.52-0.53 (m, 2H).

Example 2. Direct Preparation of Crystalline Compound 8 from Complex 7

This example illustrates the preparation of a crystalline form of (2S,3R,4R,5S,6R)-2-(4-chloro-3-(4-(2-cyclopropoxyethoxy) benzyl)phenyl)-6-(hydroxymethyl)tetrahydro-2H-pyran-3,4,5-triol.

completed the reaction was stirred continuously at 80 rpm for another 5 h. The reaction mixture was filtered over medium-speed filter paper and the filter cake was washed with distilled water (450 mL and then 300 mL) and dried under vacuum using an oil pump (~6 mm Hg) at 45° C. for 48 hours to give the target product as a white crystalline solid (94.2 g, 93.9% yield, purity (HPLC): 99.3%).

Example 3. Direct Preparation of Crystalline Compound 8 from Complex 7

This example illustrates alternative conditions for preparing crystalline (2S,3R, 4R, 5S, 6R)-2-(4-chloro-3-(4-(2-cyclopropoxyethoxy) benzyl)phenyl)-6-(hydroxymethyl) tetrahydro-2H-pyran-3,4,5-triol Procedure A:

A 250 mL of 4-neck flask was charged with the starting complex (10.0 g) and methanol (33.5 mL). After refluxing for 20 min with mechanical stirring a clear solution formed. Water (67.0 mL) was added slowly dropwise to it over 20 min. The reaction mixture was cooled slowly to room temperature (25° C.) in oil bath and stirred for another 3 h at room temperature. The reaction mixture was filtered by filter paper and the filter cake was washed with water (2×20 mL), dried under vacuum at 65° C. for 8 h to give a white crystalline solid. Yield: 6.0 g (89.6%)

Procedure B:

A 250 mL of 4-neck flask was charged with the starting complex (10.0 g) and methanol (33.5 mL). After stirring for

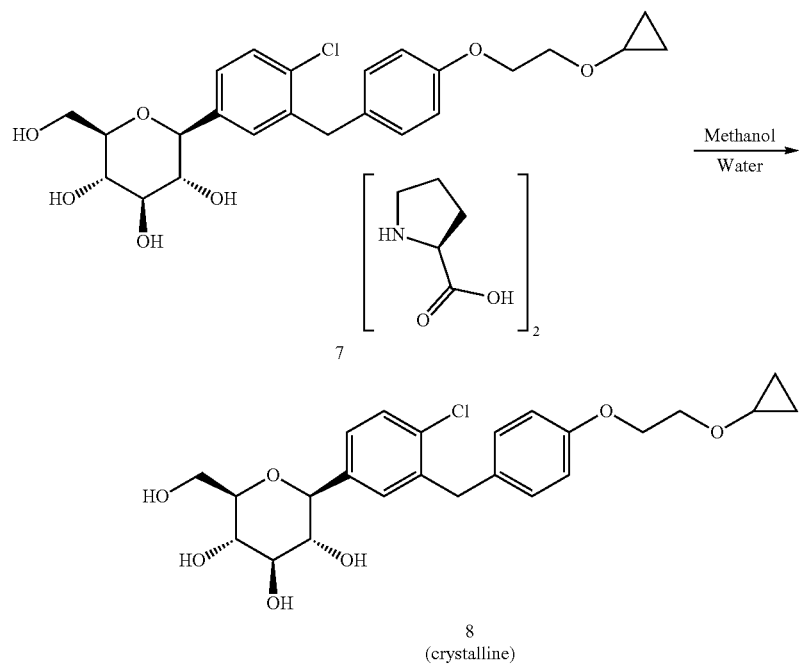

To a 5.0 L 4-necked flask equipped with a mechanical stirrer was added the starting co-crystal (150.0 g) and methanol (300 mL). The mixture was stirred at room temperature with mechanical stirring (anchor agitator, 2-blades 9 cm) until a cloudy solution/suspension formed, to which distilled water (1500 mL) was added dropwise at a rate of ~12.5 mL/min. As the mixture warmed from the exotherm of adding water to methanol, the mixture became clear after adding about ⅕ to ⅓ of the water. After the addition was 20 min with mechanical stirring, the solids did not completely dissolve. Water (67.0 mL) was added slowly dropwise to it over 20 min. At first all the remaining solids dissolved and later new crystals started to form. The reaction mixture was stirred for another 3 h at room temperature. The reaction mixture was filtered over filter paper and the filter cake was washed with water (2×20 mL), dried under vacuum at 65° C. for 8 h to give a white crystalline solid. Yield: 6.0 g (89.6%).

Procedures A and B are summarized in the table below with other conditions for preparing crystalline 8 directly from complex 7.

TABLE 1

Summary Table of Crystallization Conditions

| Complex (g) | Methanol (mL) | Water (mL) | Temp. (° C.) | Yield (%) |
|---|---|---|---|---|
| 4.0 | 20.0 | 80.0 | 70 | 87.4 |
| 10.0 | 33.5 | 67.0 | 25 | 89.6 |
| 10.0 | 33.5 | 100.0 | 25 | 91.1 |
| 10.0 | 33.5 | 67.0 | 70 | 89.6 |

Example 4. Direct Preparation of Crystalline Compound 8 from Complex 7

This example illustrates the preparation of a crystalline form of (2S,3R,4R,5S,6R)-2-(4-chloro-3-(4-(2-cyclopropoxyethoxy) benzyl)phenyl)-6-(hydroxymethyl)tetrahydro-2H-pyran-3,4,5-triol.

Compound 7 (14.0 kg) was dissolved in methanol (36.2 kg) and deionized (DI) water (11.2 kg) and then filtered. Additional DI water (41.3 kg) was added and then seed crystals were added at 35±5° C. to crystallize compound 8 from solution. Additional DI water (41.3 kg) was added to complete precipitation. The resulting slurry was filtered, and the product solids rinsed on the filter with DI water, transferred to trays, and dried under vacuum at ~65° C. to afford 8.75 kg of compound 8.

Example 5. Indirect Preparation of Crystalline Compound 8 from Complex 7

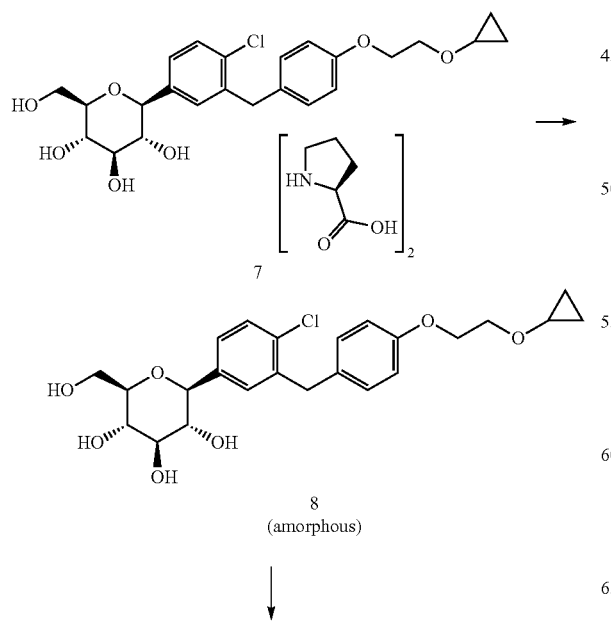

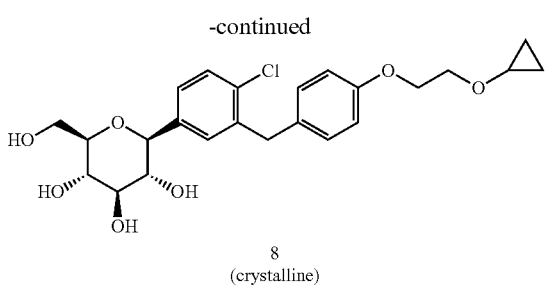

8 (crystalline)

To a 200 L glass lined reactor equipped with a double-tier paddle agitator and a glass condenser was added sequentially complex 7 (7.33 kg), ethyl acetate (67.5 kg) and pure water (74.0 kg). The mixture was heated to reflux and stirred at reflux for 30 min. The reaction mixture was cooled to approximately 50° C. and the organic layer was separated and the aqueous layer was extracted with ethyl acetate (34.0 kg). The combined organic layers were washed with pure water (3×74.0 kg) (IPC test showed that the IPC criteria for L-proline residue was met after three water washes). The mixture was concentrated at 40° C. under vacuum (~15 mmHg) for 3 h until the liquid level dropped below the lower-tier agitator paddle. The mixture (18 kg) was discharged and transferred to a 20 L rotary evaporator. The mixture was concentrated under vacuum (40° C., ~5 mmHg) to a minimum volume. The remaining trace amount of ethyl acetate was removed azeotropically at 40° C. under vacuum with methanol (10 kg). The residue was dried under vacuum of an oil pump (~6 mmHg) at 40° C. for 10 h to give 8 as a white amorphous solid (4.67 kg, purity (HPLC): 99.2%) which was used in the next step without further purification.

The recrystallization was accomplished by the following steps. To a 100 L glass line reactor equipped with a double-tier paddle agitator and a glass condenser was added the above amorphous 8 (4.67 kg) and methanol (18.0 kg). The mixture was refluxed at 70° C. for 30 min until a clear solution formed, to which pure water (45.0 kg) was added over 2 hours. After the addition was completed (the reaction temperature was 41° C.), the reaction mixture was cooled to room temperature and stirred at room temperature for 15 hours. The reaction mixture was filtered and the wet cake was washed with pure water (2×15 kg) and dried under vacuum at 55-60° C. for 12 hours to give the target product as an off-white crystalline solid (3.93 kg, yield: 84% in two steps; purity (HPLC): 99.7%).

Example 6. Direct Preparation of Crystalline Compound 8 from Amorphous 8

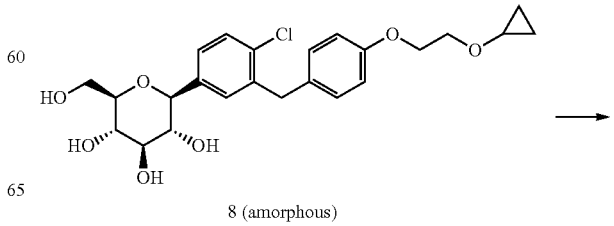

8 (amorphous)

-continued

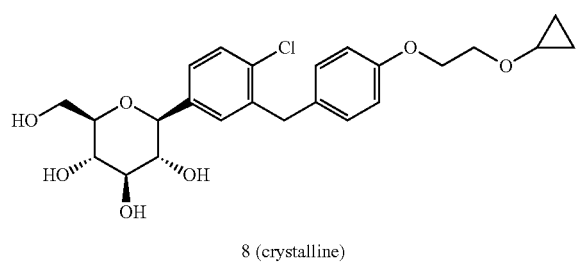

8 (crystalline)

A 5 L 4-neck flask was charged with 8 (amorphous), 116 g, and methanol (580 mL). The reaction mixture was heated to 60 C with mechanical stirring and the solution became clear. Water (2320 mL) was added dropwise to the reaction solution at 40 mL/min at 50° C. The reaction mixture was stirred overnight at room temperature. The reaction mixture was filtered and the filter cake was washed with water (2×200 mL), dried under vacuum at 55° C. for 12 hours, to afford white crystalline 8. Yield is 112.8 g (97.2%).

Example 7. Direct Preparation of Crystalline Compound 8 from Crude 6 (with Seed Crystal)

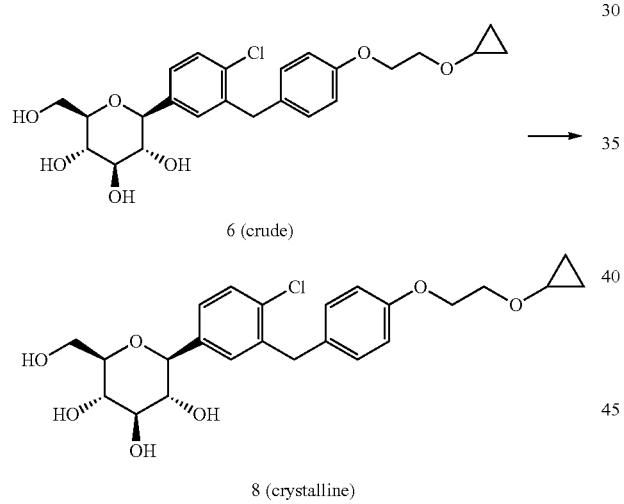

8 (crystalline)

This example illustrates the preparation of a crystalline form of (2S,3R,4R,5S,6R)-2-(4-chloro-3-(4-(2-cyclopropoxyethoxy) benzyl)phenyl)-6-(hydroxymethyl)tetrahydro-2H-pyran-3,4,5-triol.

A 250 mL 4-neck flask was charged with 6 (12.0 g, HPLC Purity: 88.3%) and methanol (48 mL). After refluxing for 30 min with magnetic stirring (120 RPM), water (72 mL) was added dropwise to the above solution over 20 min. After refluxing for another 30 min, the mixture was slowly cooled to 40 to 45° C., and seed crystal (10 mg) was added. After stirring for another 2 hours at 35 to 40° C., the mixture was cooled slowly to 20 to 25° C. and stirred for another 16 hours. The mixture was filtered and the filter cake was washed with water (2×24 mL), dried under vacuum at 60 to 65° C. for 12 hours, to afford off-white crystalline 8. Yield is 10.6 g (88.3%). HPLC Purity: 91.8%.

Example 8. Direct Preparation of Crystalline Compound 8 from Crude 6 (without Seed Crystal)

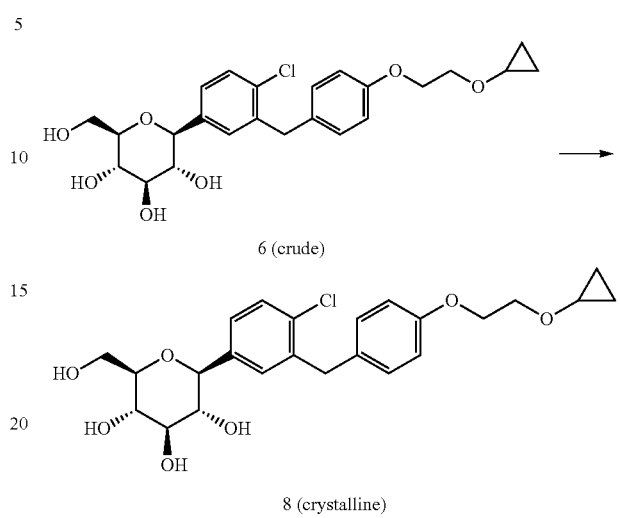

8 (crystalline)

This example illustrates the preparation of a crystalline form of (2S,3R, 4R, 5S,6R)-2-(4-chloro-3-(4-(2-cyclopropoxyethoxy) benzyl)phenyl)-6-(hydroxymethyl)tetrahydro-2H-pyran-3,4,5-triol.

A 100 mL 3-neck flask was charged with 6 (5.0 g, HPLC Purity: 90.7%) and methanol (20 mL). After refluxing for 30 min with magnetic stirring (120 RPM), water (30 mL) was added dropwise to the above solution over 20 min. After refluxing for another 30 min, the mixture was slowly cooled to 20 to 25° C. over 3 hours. After stirring for another 60 hours at 20 to 25° C., the mixture was filtered and the filter cake was washed with water (2×10 mL), dried under vacuum at 60 to 65° C. for 12 hours, to afford off-white crystalline 8. Yield is 4.3 g (86%). HPLC Purity: 92.6%.

Example 9. Preparation of Crystalline Compound 8 by Single Solvent

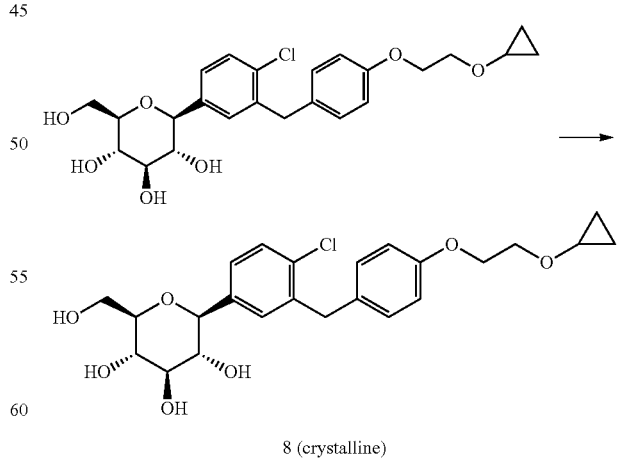

8 (crystalline)

This example illustrates the preparation of a crystalline form of (2S,3R,4R,5S,6R)-2-(4-chloro-3-(4-(2-cyclopropoxyethoxy) benzyl)phenyl)-6-(hydroxymethyl)tetrahydro-2H-pyran-3,4,5-triol.

A 40 mL glass bottle was charged with (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol (300 mg, HPLC Purity: 99.6%) and ethanol (10 mL). After shaking for 15 min at 20 to 25° C., the solid was absolutely dissolved. The solution was kept quiescence but allowed the solvent to evaporate slowly. After 2 weeks, there were only about 2 mL ethanol left and lots of needle crystals were formed. The mixture was filtered, dried under vacuum at 60 to 65° C. for 12 hours, to afford white crystalline 8. Yield is 246 mg (82%). HPLC Purity: 99.7%.

Example 10. Recrystallization of Compound 8

About 100 mg of crystalline compound 8 was dissolved with a minimal amount of solvent at about 60° C. The solution was filtrated and separated into two parts, with one part cooled in an ice bath and agitated (quick), and the other allowed to cool naturally by exposure to ambient atmosphere and temperature (slow). The solids were collected on a filter, dried and analyzed by XRPD. The table below summarizes the solvents and results of the recrystallization. All crystals formed are identical to the XRPD of the starting material.

TABLE 2

Summary of Crystallization of Compound 8 from Hot Saturated Solutions

| Solvents | Methods[1] | Results[2] |
|---|---|---|
| ACN | quick | Crystal, no change |
| | slow | Crystal, no change |
| 95% EtOH | quick | Crystal, no change |
| | slow | Crystal, no change |
| EtOAc | quick | Crystal, no change |
| | slow | Crystal, no change |
| IPA | quick | Crystal, no change |
| | slow | Crystal, no change |
| Butanol | quick | Crystal, no change |
| | slow | Crystal, no change |
| Butanone | quick | Crystal, no change |
| | slow | Crystal, no change |
| 1,4-dioxane-Heptane (1:1) | quick | Crystal, no change |
| | slow | No crystal |
| IPA-EtOAc (1:1) | quick | Crystal, no change |
| | slow | Crystal, no change |

[1]Quick = cooling in an ice bath; slow = cooling by exposure to ambient atmosphere and temperature.
[2]No change = XRPD of product identical to XRPD of starting material.

Example 11. Low Hygroscopicity of Crystalline Compound 8

The tendency toward hygroscopicity of crystalline compound 8 in powder form was tested at 75% and 92.5% relative humidity at 25° C. for up to 10 days. Reagents included: (1) water: in house, MilliQ, 18.2MΩ; (2) NaCl: AR grade; (3) KNO$_3$: AR grade; (4) saturated NaCl solution with extra NaCl solid for 25° C./75% RH control; and (5) saturated KNO$_3$ solution with extra KNO$_3$ solid for 25° C./92.5% RH control. Equipment used included (1) desiccators, 240 mm ID; and (2) weighing bottles with lids: 50 mm ID×30 mm height.

The saturated salt solutions and solids were transferred into individual desiccators, and equilibrated at 25° C. at least overnight to reach the desired relative humidity readings. Four weighing bottles were placed into each desiccator, and equilibrated overnight. The empty weighing bottles were weighed and the tare weights recorded ($W_1$). 0.5 g of crystalline compound 8 was added into three weighing bottles in each desiccator to form a thin layer with thickness of 1-2 mm. The sample weight in each bottle ($W_2$) was recorded. One empty weighing bottle was used for blank calibration. The bottles were left in each desiccator with lids open. The lids were closed and each bottle accurately weighed on days 1, 5 and 10 ($W_3$). The bottles were returned to each desiccator with lids open immediately after weighing.

The following formula was used to calculate the weight increase:

$$\text{Weight Increase \%} = \frac{W_3 - W_1 - W_2 - W_B}{W_2} \times 100\%$$

$W_B$=the weight increase of empty weighing bottle.

TABLE 3

Test results of crystal compound 8 at 25° C./75% RH.

| wt | Empty bottle | Sample Weight | Appearance | Bottle + Sample | Sample Weight | Weight Increase | Appearance |
|---|---|---|---|---|---|---|---|
| | | Initial | | | | 1 day | |
| 1 | 30.36142 | 0.50434 | White powder | 30.86727 | 0.50585 | 0.32914% | White powder |
| 2 | 32.96588 | 0.50631 | White powder | 33.47323 | 0.50735 | 0.23503% | White powder |
| 3 | 31.27798 | 0.50066 | White powder | 31.77934 | 0.50136 | 0.16978% | White powder |
| Blank | 31.92783 | | | 31.92768 | −0.00015 | | |
| Average | | | | | | 0.24465% | |
| | | | | | | 5 days | |
| 1 | | | | 30.86648 | 0.50506 | 0.10509% | White powder |
| 2 | | | | 33.47339 | 0.50751 | 0.19948% | White powder |
| 3 | | | | 31.77962 | 0.50164 | 0.15779% | White powder |
| Blank | | | | 31.92802 | 0.00019 | | |
| Average | | | | | | 0.15412% | |

TABLE 3-continued

Test results of crystal compound 8 at 25° C./75% RH.

| wt | Empty bottle | Sample Weight | Appearance | Bottle + Sample | Sample Weight | Weight Increase | Appearance |
|---|---|---|---|---|---|---|---|
| | | | | | | 10 days | |
| 1 | | | | 30.86738 | 0.50596 | 0.35095% | White powder |
| 2 | | | | 33.47321 | 0.50733 | 0.23108% | White powder |
| 3 | | | | 31.77947 | 0.50149 | 0.19574% | White powder |
| Blank | | | | 31.92768 | −0.00015 | | |
| Average | | | | | | 0.25926% | |

TABLE 4

Test results of crystal compound 8 at 5° C./92.5% RH.

| | Empty bottle | Sample Weight | Appearance | Bottle + Sample | Sample Weight | Weight Increase | Appearance |
|---|---|---|---|---|---|---|---|
| | | Initial | | | | 1 day | |
| 1 | 34.11948 | 0.50356 | White powder | 34.62330 | 0.50382 | 0.05362% | White powder |
| 2 | 30.13094 | 0.50215 | White powder | 30.63360 | 0.50266 | 0.10355% | White powder |
| 3 | 33.01277 | 0.50546 | White powder | 33.51923 | 0.50646 | 0.19982% | White powder |
| Blank | 40.35822 | | | 40.35821 | −0.00001 | | |
| Average | | | | | | 0.11900% | |
| | | | | | | 5 days | |
| 1 | | | | 34.62358 | 0.50410 | 0.04170% | White powder |
| 2 | | | | 30.63446 | 0.50352 | 0.20711% | White powder |
| 3 | | | | 33.51977 | 0.50700 | 0.23939% | White powder |
| Blank | | | | 40.35855 | 0.00033 | | |
| Average | | | | | | 0.16273% | |
| | | | | | | 10 days | |
| 1 | | | | 34.62472 | 0.50524 | 0.26015% | White powder |
| 2 | | | | 30.63428 | 0.50334 | 0.16330% | White powder |
| 3 | | | | 33.51994 | 0.50717 | 0.26511% | White powder |
| Blank | | | | 40.35859 | 0.00037 | | |
| Average | | | | | | 0.22952% | |

The weight increases of crystalline compound 8 in powder samples at 75% and 92.5% relative humidity at 25° C. for 10 days were below 0.26%. Thus, crystalline compound 8 in powder form exhibited low hygroscopicity at the study conditions.

Example 12. Preparation of Capsules Containing Crystalline Compound 8

To prepare capsules containing crystalline compound 8, the compound and silicified microcrystalline cellulose (Prosolv HD90) were blended and then sifted through a #30 sieve into a polyethylene bag. A portion of the crystalline compound 8/Prosolv HD90 blend was removed. Magnesium stearate was sifted through a #30 sieve into this portion and the mixture blended. The 3-component portion was returned to the larger compound 8/Prosolv HD90 blend, and the mixture further blended. The final blend was put into a polyethylene bag. Empty capsule shells (Size 2) were weighed to determine the average capsule weight. The final blend in the polyethylene bag was fed onto an MG2 Planeta encapsulator and approximately 100 mg of final blend was loaded into each capsule. About every 5 to 10 minutes, loaded capsules were sampled for acceptable fill weight. This was achieved by sampling 10 loaded capsules, weighing each loaded capsule and comparing the results to the theoretical average weight of a capsule plus the targeted 100 mg load of blend. Another 10 capsules were visually inspected for cracks, chips, dents, splits unexpected marks, and closures. If necessary, the encapsulation and blend loading process can be adjusted to maintain proper target weight fill into the capsules. Acceptable capsules were placed in a double lined polyethylene bag for further processing. Loaded capsules were weight sorted electronically, with low and high weigh filled capsules rejected, and acceptable weight filled capsules forwarded for further processing. Acceptable weight checked capsules were polished and placed in double polyethylene bags.

TABLE 5

Components of 20 mg Capsules with Crystalline 8

| Component | Amount per unit (mg/capsule) | Function | Quality Standard |
|---|---|---|---|
| Crystalline Compound 8 | 20.00 | Active Ingredient | In house |
| Silicified Microcrystalline Cellulose (Prosolv ® HD90) | 79.40 | Glidant and Hydrophilic Matrix | USP/NF; Ph. Eur., JP. |

TABLE 5-continued

Components of 20 mg Capsules with Crystalline 8

| Component | Amount per unit (mg/capsule) | Function | Quality Standard |
|---|---|---|---|
| Magnesium Stearate (HyQual ®, Vegetable Grade) | 0.60 | Lubricant | USP/NF; Ph. Eur., JP |
| Size 2, Gelatin, White, Coni-Snap ® (0999) Opaque Body and Cap | 1 | Capsule Shell | In house |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A crystalline form of the compound of the formula:

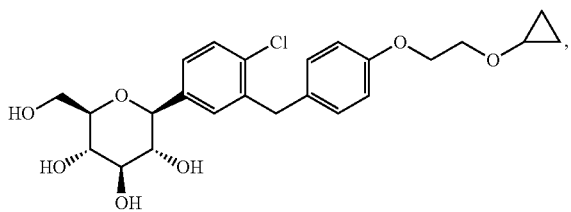 [SMILES: OC[C@H]1O[C@@H](c2ccc(Cl)c(Cc3ccc(OCCOC4CC4)cc3)c2)[C@H](O)[C@@H](O)[C@@H]1O]

characterized by a Raman spectra that comprises three or more peaks at about 353, 688, 825, 1178, 1205, 1212, 1608, 2945, 3010 and 3063 cm$^{-1}$.

2. The crystalline form in accordance with claim 1, characterized by a Raman spectra that comprises peaks at about 353, 688, and 825 cm$^{-1}$.

3. The crystalline form in accordance with claim 1, characterized by a Raman spectra that comprises peaks at about 1178, 1205, and 1212 cm$^{-1}$.

4. The crystalline form in accordance with claim 1, characterized by a Raman spectra that comprises peaks at about 1608, 2945, 3010 and 3063 cm$^{-1}$.

5. The crystalline form in accordance with claim 1, characterized by a Raman spectra that comprises peaks at about 353, 688, 825, 1608, 2945, 3010 and 3063 cm$^{-1}$.

6. The crystalline form in accordance with claim 1, characterized by a Raman spectra that comprises peaks at about 1178, 1205, 1212, 1608, 2945, 3010 and 3063 cm$^{-1}$.

7. The crystalline form in accordance with claim 1, characterized by a Raman spectra that comprises peaks at about 353, 688, 825, 1178, 1205, and 1212 cm$^{-1}$.

8. The crystalline form in accordance with claim 1, characterized by the Raman peaks substantially in accordance with those of FIG. 4.

9. A pharmaceutical composition comprising a pharmaceutically acceptable excipient and a crystalline form of the compound of claim 1.

10. The crystalline form in accordance with claim 1, characterized by a Raman spectra that comprises peaks at about at about 353, 688, 825, 1178, 1205, 1212, 1608, 2945, 3010 and 3063 cm$^{-1}$.

* * * * *